United States Patent
Xiao

(10) Patent No.: US 8,839,659 B2
(45) Date of Patent: Sep. 23, 2014

(54) SENSORS AND DEVICES CONTAINING ULTRA-SMALL NANOWIRE ARRAYS

(75) Inventor: Zhili Xiao, Naperville, IL (US)

(73) Assignee: Board of Trustees of Northern Illinois University, DeKalb, IL (US)

(*) Notice: Subject to any disclaimer, the term of this patent is extended or adjusted under 35 U.S.C. 154(b) by 1 day.

(21) Appl. No.: 13/245,674

(22) Filed: Sep. 26, 2011

(65) Prior Publication Data

US 2012/0085145 A1    Apr. 12, 2012

Related U.S. Application Data

(60) Provisional application No. 61/391,195, filed on Oct. 8, 2010.

(51) Int. Cl.
| | |
|---|---|
| *G01N 27/04* | (2006.01) |
| *H01M 4/92* | (2006.01) |
| *B82Y 15/00* | (2011.01) |
| *B82B 1/00* | (2006.01) |
| *G01N 33/00* | (2006.01) |
| *G01N 27/12* | (2006.01) |
| *B82Y 30/00* | (2011.01) |

(52) U.S. Cl.
CPC ............ *G01N 27/127* (2013.01); *G01N 33/005* (2013.01); *B82Y 30/00* (2013.01); *Y10S 977/932* (2013.01); *Y10S 977/948* (2013.01); *Y10S 977/957* (2013.01); *Y10S 977/762* (2013.01); *Y10S 977/81* (2013.01)
USPC .......... 73/31.06; 977/932; 977/948; 977/957; 977/762; 977/810; 420/463; 428/401

(58) Field of Classification Search
USPC ............ 73/23.2, 31.05, 31.06; 977/762, 810, 977/948, 953, 957; 420/463; 428/401
See application file for complete search history.

(56) References Cited

U.S. PATENT DOCUMENTS

| | | | |
|---|---|---|---|
| 4,058,368 A | | 11/1977 | Svensson et al. |
| 6,231,744 B1 * | | 5/2001 | Ying et al. ................... 205/324 |
| 7,171,841 B2 | | 2/2007 | Xu et al. |

(Continued)

FOREIGN PATENT DOCUMENTS

| | | |
|---|---|---|
| EP | 1 426 756 | 6/2004 |
| EP | 2 362 216 | 8/2011 |

(Continued)

OTHER PUBLICATIONS

D. Wang, B. A. Sheriff, M. McAlpine, J. R. Heath, "Development of Ultra-High Density Silicon Nanowire Arrays for Electronics Applications," Nano Res (2008) 1: 9-21.*

(Continued)

*Primary Examiner* — Lisa Caputo
*Assistant Examiner* — Punam Roy
(74) *Attorney, Agent, or Firm* — Evan Law Group LLC

(57) ABSTRACT

A network of nanowires may be used for a sensor. The nanowires are metallic, each nanowire has a thickness of at most 20 nm, and each nanowire has a width of at most 20 nm. The sensor may include nanowires comprising Pd, and the sensor may sense a change in hydrogen concentration from 0 to 100%. A device may include the hydrogen sensor, such as a vehicle, a fuel cell, a hydrogen storage tank, a facility for manufacturing steel, or a facility for refining petroleum products.

21 Claims, 17 Drawing Sheets

(56) References Cited

U.S. PATENT DOCUMENTS

| | | | |
|---|---|---|---|
| 7,179,561 B2* | 2/2007 | Niu et al. | 429/409 |
| 7,186,381 B2 | 3/2007 | Penner et al. | |
| 8,187,865 B2* | 5/2012 | Yun et al. | 435/287.2 |
| 2003/0008505 A1* | 1/2003 | Chen et al. | 438/689 |
| 2003/0072885 A1 | 4/2003 | Lee et al. | 427/294 |
| 2004/0106203 A1* | 6/2004 | Stasiak et al. | 436/49 |
| 2004/0118698 A1* | 6/2004 | Lu et al. | 205/224 |
| 2004/0146735 A1* | 7/2004 | Weiner et al. | 428/606 |
| 2005/0247961 A1* | 11/2005 | Zhou | 257/213 |
| 2006/0046480 A1* | 3/2006 | Guo | 438/685 |
| 2006/0131695 A1* | 6/2006 | Kuekes et al. | 257/618 |
| 2006/0263255 A1 | 11/2006 | Han et al. | |
| 2006/0289351 A1* | 12/2006 | Xiao et al. | 210/500.25 |
| 2007/0040191 A1* | 2/2007 | Bezryadin et al. | 257/213 |
| 2007/0077429 A1* | 4/2007 | Mirkin et al. | 428/402 |
| 2007/0087470 A1* | 4/2007 | Sunkara et al. | 438/99 |
| 2007/0209576 A1* | 9/2007 | Sunkara et al. | 117/87 |
| 2008/0078234 A1* | 4/2008 | Monty et al. | 73/31.05 |
| 2008/0206555 A1* | 8/2008 | Choi et al. | 428/332 |
| 2009/0017363 A1* | 1/2009 | Niu et al. | 429/44 |
| 2009/0035525 A1* | 2/2009 | Garcia et al. | 428/156 |
| 2009/0084159 A1* | 4/2009 | Sun et al. | 73/31.05 |
| 2009/0233086 A1* | 9/2009 | Hirai | 428/328 |
| 2010/0005853 A1* | 1/2010 | Visel et al. | 73/19.07 |
| 2010/0200199 A1* | 8/2010 | Habib et al. | 165/104.26 |
| 2010/0269569 A1* | 10/2010 | Yang et al. | 73/31.06 |
| 2011/0189510 A1* | 8/2011 | Caracciolo et al. | 429/50 |
| 2011/0274882 A1* | 11/2011 | Wallace et al. | 428/166 |
| 2011/0275005 A1* | 11/2011 | Zhu et al. | 429/482 |
| 2012/0034410 A1* | 2/2012 | Baumgart et al. | 428/80 |
| 2012/0036919 A1* | 2/2012 | Kamins et al. | 73/31.05 |
| 2012/0094192 A1* | 4/2012 | Qu et al. | 429/336 |
| 2012/0134880 A1* | 5/2012 | Kurkina et al. | 422/82.01 |
| 2012/0147587 A1* | 6/2012 | Wober | 362/84 |
| 2012/0282540 A1* | 11/2012 | Niu et al. | 429/483 |

FOREIGN PATENT DOCUMENTS

| | | |
|---|---|---|
| KR | 20090007443 | 1/2009 |
| KR | 100959245 | 5/2010 |
| WO | 2008/153593 | 12/2008 |
| WO | 2012/047869 | 4/2012 |

OTHER PUBLICATIONS

N. Ebrahimi, K. McCullough, Z. Xiao, "Reliability of sensors based on nanowire networks," IIE Transactions (2013) 45: 215-228.*
Y. Du, L. Shi, T. He, X. Sun, Y. Mo, "SERS enhancement dependence on the diameter and aspect ratio of silver-nanowire array fabricated by anodic aluminum oxide template," Applied Surface Science (2008) 225: 1901-1905.*
Lin, C. et al., "An in situ electrical study on primary hydrogen spillover from nanocatalysts to amorphous carbon support", Applied Physics Letters, vol. 93, pp. 233110-1-233110-3, (2008).
Ramanathan, M. et al., "Crossover behavior in the hydrogen sensing mechanism for palladium ultrathin films", Nanotechnology, vol. 21, pp. 125501-1-125501-6, (2010).
U.S. Department of Energy, "Fuel cell technologies program multi-year research, development and demonstration plan", found at www1.eere.energy.gov/hydrogenandfuelcells/mypp/index.html, printed on Feb. 15, 2012.
Tabib-Azar, M. et al., "Highly sensitive hydrogen sensors using palladium coated fiber optics with exposed cores and evanescent field interactions", SPIE, Microelectronic Structures and MEMS for Optical Processing IV, proceedings vol. 3513, pp. 80-88, (1998).
Crabtree, G.W. "The hydrogen economy", Physics Today, vol. 57, pp. 39-44, (2004).
Jardine, A.P. "Hydrogen sensors for hydrogen fuel cell applications", Darnell Group, pp. 1-4, found at www.powerpulse.net/techPaper.php?paperID=99, printed on Feb. 14, 2012.
Buttner, W.J. et al., "An overview of hydrogen safety sensors and requirements", International Journal of Hydrogen Energy, vol. 36, pp. 2462-2470, (2011).
Kong, J. et al., "Functionalized carbon nanotubes for molecular hydrogen sensors", Advanced Materials, vol. 13, No. 18, pp. 1384-1386, (2001).
Favier, F. et al., "Hydrogen sensors and switches from electrodeposited palladium mesowire arrays", Science, vol. 293, issue 5538, pp. 2227-2231, (2001).
Walter, E.C. et al., "Palladium mesowire arrays for fast hydrogen sensors and hydrogen-actuated switches", Analytical Chemistry, vol. 74, No. 7, pp. 15461553, (2002).
Tibuzzi, A. et al., "Polysilicon mesoscopic wires coated by Pd as high sensitivity H2 sensors", Sensors and Actuators B, vol. 83, pp. 175-180, (2002).
Varghese, O.K. et al., "Extreme changes in the electrical resistance of titania nanotubes with hydrogen exposure", Advanced Materials, vol. 15, No. 7-8, pp. 624-627, (2003).
Varghese, O.K. et al., "Hydrogen sensing using titania nanotubes", Sensors and Actuators B, vol. 93, pp. 338-344, (2003).
Xu, T. et al., "Self-assembled monolayer-enhanced hydrogen sensing with ultrathin palladium films", Applied Physics Letters, vol. 86, pp. 203104-1-203104-3, (2005).
Paulose, M. et al., "Unprecedented ultra-high hydrogen gas sensitivity in undoped titania nanotubes", Nanotechnology, vol. 17, pp. 398-402, (2006).
Ding, D. et al., "Volume-expansion-enhanced pinning of nanoporous Pd films for detection of high-concentration hydrogen", Sensor Letters, vol. 4, pp. 331-333, (2006).
Ding, D. et al., "A pyrolytic, carbon-stabilized, nanoporous Pd film for wide-range $H_2$ sensing", Advanced Materials, vol. 19, pp. 1996-1999, (2007).
Khanuja, M. et al., "Pulse like hydrogen sensing response in Pd nanoparticle layers", Applied Physics Letters, vol. 91, pp. 253121-1-253121-3, (2007).
van Lith, J. et al., "A hydrogen sensor based on tunneling between palladium clusters", Applied Physics Letters, vol. 91, pp. 181910-1-181910-3, (2007).
Sun, Y. et al., "High-performance, flexible hydrogen sensors that use carbon nanotubes decorated with palladium nanoparticles", Advanced Materials, vol. 19, pp. 2818-2823, (2007).
Kiefer, T. et al., "A single nanotrench in a palladium microwire for hydrogen detection", Nanotechnology, vol. 19, pp. 125502-1-125502-9, (2008).
Joshi, R.K. et al., "Pd nanoparticles and thin films for room temperature hydrogen sensor" Nanoscale Research Letters, vol. 4, pp. 1191-1196, (2009).
Yang, F. et al., "Fast, sensitive hydrogen gas detection using single palladium nanowires that resist fracture", Nano Letters, vol. 9, No. 5, pp. 2177-2182, (2009).
Jean, K.J. et al., "Finite size effect on hydrogen gas sensing performance in single Pd nanowires", Nanotechnology, vol. 19, pp. 495501-1-495501-6, (2008).
Offermans, P. et al., "Ultralow-power hydrogen sensing with single palladium nanowires", Applied Physics Letters, vol. 94, pp. 223110-1-223110-3, (2009).
Khanuja, M. et al., "Concentration-specific hydrogen sensing behavior in monosized Pd nanoparticle layers", Nanotechnology, vol. 20, pp. 015502-1-015502-7, (2009).
Yang, F. et al., "Joule heating a palladium nanowire sensor for accelerated response and recovery to hydrogen gas", Small, vol. 6, No. 13, pp. 1422-1429, (2010).
Yang, F. et al., "Smaller is faster and more sensitive: the effect of wire size on the detection of hydrogen by single palladium nanowires", ACS Nano, vol. 4, No. 9, pp. 5233-5244, (2010).
Agar, P. et al., "Sensing response of palladium nanoparticles and thin films to deuterium and hydrogen: Effect of gas atom diffusivity", Sensors and Actuators B: Chemical, vol. 150, pp. 686-691, (2010).
Kiefer, T. et al., "The transition in hydrogen sensing behavior in noncontinuous palladium films", Applied Physics Letters, vol. 97, pp. 121911-1-121911-3, (2010).
Kiefer, T. et al., "Fast and robust hydrogen sensors based on discontinuous palladium films on polyimide, fabricated on a wafer scale", Nanotechnology, vol. 21, pp. 505501-1-505501-5, (2010).

(56) References Cited

OTHER PUBLICATIONS

Zou, J. et al., "Hydrogen-induced reversible insulator-metal transition in a palladium nanosphere sensor", Small, vol. 6, No. 21, pp. 2358-2361, (2010).
Sekhar, P.K. et al., "Development and testing of a miniaturized hydrogen safety sensor prototype", Sensors and Actuators B: Chemical, vol. 148, pp. 469-477, (2010).
Lee, J.M. et al., "Effects of surface roughness on hydrogen gas sensing properties of single Pd nanowires", Journal of Nanoscience and Nanotechnology, vol. 11, pp. 2151-2154, (2011).
Kim, K.R. et al., "Suppression of phase transitions in Pd thin films by insertion of a Ti buffer layer", Journal of Material Science, vol. 46, pp. 1597-1601, (2011).
Noh, J-S. et al., "Low-dimensional palladium nanostructures for fast and reliable hydrogen gas detection", Sensors, vol. 11, pp. 825-851, (2011).
Zeng, X.Q. et al., "Hydrogen gas sensing with networks of ultrasmall palladium nanowires formed on filtration membranes", Nano Letters, vol. 11, pp. 262-268, (2011).
Knight, B. et al., "Development of sensors for automotive PEM-based fuel cells", United Technologies Corporation, Fuel Cells Division, 243 pages, found at www.lanl.gov/orgs/mpa/mpa11/FinalReportforDOESensorsContractUTRC.pdf, (2005).
Liu, R-J. et al., "In situ electron microscopy studies of the sintering of palladium nanoparticles on alumina during catalyst regeneration processes", Microscopy and Microanalysis, vol. 10, pp. 77-85, (2004).
Baker, R.T.K. et al., "The interaction of palladium with alumina and titanium-oxide supports", Journal of Catalysis, vol. 89, pp. 422-432, (1984).
Xiao, Z.L. et al., "Fabrication of alumina nanotubes and nanowires by etching porous alumina membranes", Nano Letters, vol. 2, No. 11, pp. 1293-1297, (2002).
Crispin R.M. et al., "The wetting and bonding behaviour of some nickel alloy-alumina systems", Journal of Materials Science, vol. 11, pp. 17-21, (1976).
Asthana, R. et al., "Wettability and interface considerations in advanced heat-resistant Ni-base composites", Bulletin of the Polish Academy of Sciences, Technical Sciences, vol. 54, No. 2, pp. 147-166, (2006).
Welp, U. et al., "Superconducting transition and vortex pinning in Nb films patterned with nano-scale hole-arrays", Physical Review B., vol. 66, pp. 212507-1-212507-17, (2002).
Xiao, Z.L. et al., "Nickel antidot arrays on alumina substrates", Applied Physics Letters, vol. 81, No. 15, pp. 2869-2871, (2002).
Kulkarni, A.K. et al., "Electrical and structural characteristics of chromium thin films deposited on glass and alumina substrates", Thin Solid Films, vol. 301, pp. 17-22, (1997).
Matula, R.A. "Electrical resistivity of copper, gold, palladium, and silver", Journal of Physical Chemistry Reference Data, vol. 8, No. 4, pp. 1147-1298, (1979).
Ealet, B. et al., "A surface analytical study of the formation and adhesion of chromium films on alumina", Journal of Adhesion Science and Technology, vol. 6, No. 11, pp. 1221-1231, (1992).
Sakamoto, Y. et al., "Electrical resistance measurements as a function of composition of palladium-hydrogen (deuterium) systems by a gas phase method", Journal of Physics: Condensed Matter, vol. 8, pp. 3399-3411, (1996).
Suleiman, M. et al., "Phase transition and lattice expansion during hydrogen loading of nanometer sized palladium clusters", Journal of Alloys and Compounds, vol. 356-357, pp. 644-648, (2003).
Sachs, C. et al., "Solubility of hydrogen in single-sized palladium clusters", Physical Review B, vol. 64, pp. 075408-1-075408-10, (2001).
Di Vece, M. et al., "Hydrogen-induced ostwald ripening at room temperature in a Pd nanocluster film", Physical Review Letters, vol. 100, pp. 236105-1-236105-4, (2008).
Liekhus, K.J. et al., "Flammability of gas mixtures containing volatile organic compounds and hydrogen", Journal of Loss Prevention in the Process Industries, vol. 13, issues 3-5, pp. 377-384, (2000).

"Hydrogen Leak Detector for Vehicle Fuel Cell Applications", pp. 1-3, found at www.fuelcellsensor.com, printed on Feb. 15, 2012.
Bodzenta, J. et al., "Thin palladium film as a sensor of hydrogen gas dissolved in transformer oil", Sensors and Actuators B, vol. 87, pp. 82-87, (2002).
Christofides, C. et al., "Solid-state sensors for trace hydrogen gas detection", Journal of Applied Physics, vol. 68, No. 6, pp. R1-R30, (1990).
Chen, H-I. et al., "A novel high-sensitive Pd/InP hydrogen sensor fabricated by electroless plating", Sensors and Actuators B, vol. 85, pp. 10-18, (2002).
Wang, C. et al., "Detectivity comparison between thin-film Pd/PVDF photopyroelectric interferometric and optical reflectance hydrogen sensors", Review of Scientific Instruments, vol. 70, No. 11, pp. 4370-4376, (1999).
Sutapun, B. et al., "Pd-coated elastooptic fiber optic Bragg grating sensors for multiplexed hydrogen sensing", Sensors and Actuators B, vol. 60, pp. 27-34, (1999).
Pundt, A. "Hydrogen in nano-sized metals", Advanced Engineering Materials, vol. 6, No. 1-2, pp. 11-21, (2004).
Lee, E. et al., "Hysteresis behavior of electrical resistance in Pd thin films during the process of absorption and desorption of hydrogen gas", International Journal of Hydrogen Energy, vol. 35, pp. 6984-6991, (2010).
Jeon, K.J. et al., "Individual Pd nanowire hydrogen sensors fabricated by electron-beam lithography", Nanotechnology, vol. 20, pp. 135502-1-135502-5, (2009).
Yu, S. et al., "Fabrication of palladium nanotubes and their application in hydrogen sensing", Chem. Mater., vol. 17, No. 13, pp. 3445-3450, (2005).
Menke, E.J. et al., "Lithographically patterned nanowire electrodeposition", Nature Materials, vol. 5, pp. 914-919, (2006).
"The Anopore inorganic membrane", found at www.whatman.com/PRODAnoporeInorganicMembranes.aspx., 3 pages, (2009).
Narehood, D.G. et al., "X-ray diffraction and H-storage in ultra-small palladium particles", International Journal of Hydrogen Energy, vol. 34, pp. 952-960, (2009).
Eastman, J.A. et al., "Narrowing of the palladium-hydrogen miscibility gap in nanocrystalline palladium", Physical Review B, vol. 48, No. 1, pp. 84-93, (1993).
Hughes, R.C. et al., "Thin films of Pd/Ni alloys for detection of high hydrogen concentrations", Journal of Applied Physics, vol. 71, No. 1, pp. 542-544, (1992).
Ding, D. et al., "Hydrogen sensing of nanoporous palladium films supported by anodic aluminum oxides", Sensors and Actuators B, vol. 120, pp. 182-186, (2006).
Hakamada, M. et al., "Hydrogen storage properties of nanoporous palladium fabricated by dealloying", Journal of Physical Chemistry C, vol. 114, pp. 868-873, (2010).
NIU Media Relations & Internal Communications, "NIU scientists find fast, easy way to make hydrogen nanosensors", found at www.niu.edu/mediarelations/news/2011/01/hydrogen_nano.shtml, 1 page, Jan. 12, 2011.
Zeng, X-Q. et al., "Networks of ultrasmall Pd/Cr nanowires as high performance hydrogen sensors", ACS Nano, vol. 5, No. 9, pp. 7443-7452, (2011).
Kim, K.T. et al., "Hydrogen gas sensor using pd nanowires electrodeposited into anodized alumina template", IEEE Sensors Journal, vol. 6, No. 3, pp. 509-513, (2006).
Lin, C. et al., "Hydrogen spillover enhanced hydriding kinetics of palladium-doped lithium nitride to lithium imide", The Journal of Physical Chemistry C, vol. 113, No. 19, pp. 8513-8517, (2009).
Lu, C. et al., "MOS hydrogen sensor with very fast response based on ultra-thin thermal $SiO_2$ film", International Journal of Hydrogen Energy, vol. 35, pp. 12561-12567, (2010).
Thomas, R.C. et al., "Sensors for detecting molecular hydrogen based on Pd metal alloys", Journal of the Electrochemical Society, vol. 144, No. 9, pp. 3245-3249, (1997).
International Search Report dated Apr. 2, 2012 for PCT application No. PCT/US2011/054742.

(56) References Cited

OTHER PUBLICATIONS

Srinivasan, U. et al., "Alkyltrichlorosilane-based self-assembled monolayer films for stiction reduction in silicon micromachines", Journal of Microelectromechanical Systems, vol. 7, issue 2, pp. 252-260, (1998).

Zeng, X.Q. et al., "Hydrogen responses of ultrathin Pd films and nanowire networks with a Ti buffer layer", Journal of Materials Science, vol. 47, pp. 6447-6651, (2012).

Ali, M., et al. "Pt/GaN Schottky diodes for hydrogen gas sensors", Sensors and Actuators B: Chemical, vol. 113, No. 2, pp. 797-804, (2006).

Neudeck, P.G. et al., "Hydrogen gas sensors fabricated on atomically flat 4H-SiC webbed cantilevers", Materials Science Forum, vols. 600-603, pp. 1199-1202, (2009).

Kocanda, M. et al., "Detection of cyclic volatile organic compounds using single-step anodized nanoporous alumina sensors", IEEE Sensors Journal, vol. 9, No. 7, pp. 836-841, (2009).

Kocanda, M. et al., "Enhanced hydrogen sensing employing electrodeposited palladium nanowires enclosed in anodized aluminum oxide nanopores", IEEE Sensors Conference, pp. 308-311, (2009).

Syaifudin, A.R.M. et al., "Measurements and performance evaluation of novel interdigital sensors for different chemicals related to food poisoning", IEEE Sensors Journal, vol. 11, No. 11, pp. 2957-2965, (2011).

Syaifudin, A.R.M. et al., "Modelling and fabrication of optimum structure of novel interdigital sensors for food inspection", International Journal of Numerical Modelling: Electronic Networks, Devices and Fields, vol. 25, issue 1, pp. 64-81, (2012).

Syaifudin, A.R.M. et al., "A low cost novel sensing system for detection of dangerous marine biotoxins in seafood", Sensors and Actuators B: Chemical, vol. 137, issue 1, pp. 67-75, (2009).

Wang, D. et al., "Development of ultra-high density silicon nanowire arrays for electronics applications", Nano Research, vol. 1, pp. 9-21, (2008).

Ebrahimi, N. et al., "Reliability of sensors based on nanowire networks", IIE Transactions, vol. 45, No. 2, pp. 215-228, (2013).

Du, Y. et al., "SERS enhancement dependence on the diameter and aspect ratio of silver-nanowire array fabricated by anodic aluminum oxide template", Applied Surface Science, vol. 255, pp. 1901-1905, (2008).

Kumar, M.K. et al., "Palladium dispersed multiwalled carbon nanotube based hydrogen sensor for fuel cell applications", International Journal of Hydrogen Energy, vol. 32, issue 13, pp. 2518-2526, (2007).

Pavlovsky, I. et al., "Palladium nanoparticles hydrogen sensor", Sensors & Transducers Journal, vol. 73, issue 11, pp. 793-798, (2006).

Mubeen, S. et al., "Palladium nanoparticles decorated single-walled carbon nanotube hydrogen sensor", Journal of Physical Chemistry C, vol. 111, No. 17, pp. 6321-6327, (2007).

Product description for "MNPS-B Hydrogen Sensor", Applied Nanotech, Inc., 3 pages, (2009).

* cited by examiner

SENSORS AND DEVICES CONTAINING ULTRA-SMALL NANOWIRE ARRAYS

REFERENCE TO RELATED APPLICATIONS

This application claims the benefit of U.S. Provisional Application No. 61/391,195 entitled "HYDROGEN GAS DETECTION WITH NETWORKS OF ULTRA-SMALL NANOWIRES AND NANOCLUSTERS OF PURE PALLADIUM, PALLADIUM ALLOYS, AND PALLADIUM MULTILAYERS" filed 8 Oct. 2010.

FEDERALLY SPONSORED RESEARCH OR DEVELOPMENT

This invention was made with government support under Department of Energy (DOE) Grant No. DE-FG02-06ER46334. The government has certain rights in the invention.

BACKGROUND

Hydrogen ($H_2$) gas has many uses. For example, it is the main propellant in spaceships and commercial and military launch vehicles. It is also used extensively in scientific research and industry, notably in the manufacturing of glass and steel as well as in the refining of petroleum products.[1] In 2003 the U.S. Department of Energy accelerated its hydrogen program to develop the technology needed for commercially viable hydrogen-powered fuel cells—a way to power cars, trucks, homes, and businesses that could significantly reduce pollution and greenhouse gas emissions as well as our dependence on fossil fuels.[2] However, $H_2$ gas is highly volatile and, when in contact with oxygen, can become extremely flammable and highly explosive. The use of effective $H_2$ sensors to accurately and quickly respond to $H_2$ gas leaks and to monitor manufacturing and distribution will be crucial for the safe deployment of all $H_2$-based applications. For example, $H_2$ gas detection in commercial and military launch vehicles is a great concern at both the propellant filling ground-support station and within the common booster core during ground operations.[3] Fuel cells[4] at the core of hydrogen-powered cars require two types of $H_2$ sensors: sensors to monitor the quality of the hydrogen feed gas and, more importantly, sensors to detect leaks. These $H_2$ sensors must be sensitive enough to discriminate between ambient low-level traces of hydrogen and those that are generated by a $H_2$ leak.[5]

A crucial parameter of $H_2$ sensors in many applications is the response time. For example, the sensors that analyze $H_2$ content in a mixed gas and monitor the reaction process require extremely short response times to follow the fuel cell's power generation and to shut down the engine in the event of a tank rupture. Currently, commercial sensors suffer from longer response times than the duty cycles likely needed for most applications.[5,6]

Pd based $H_2$ sensors have a unique advantage in that the surface of palladium can act catalytically to break the H—H bond in diatomic hydrogen, allowing monatomic hydrogen to diffuse into the material. Furthermore, palladium can dissolve more than 600 times its own volume of hydrogen, but dissolves little of the other common gases such as nitrogen, oxygen, nitrogen monoxide, carbon dioxide, and carbon monoxide. This allows Pd to be the most selective $H_2$ sensing material.[6] Finally, the Pd hydrogenation process is reversible at room temperature, enabling simpler designs and allowing for less power consumption by avoiding heating to achieve elevated temperatures.

In the presence of $H_2$ the resistance of Pd will change due to the formation of a solid solution of Pd/H (at low $H_2$ pressure, $\alpha$-phase) or a hydride (at high $H_2$ pressure, $\beta$-phase). The level of dissolved hydrogen changes the electrical resistivity of the metal and also its volume due to the formation of metal hydride. Thus, Pd is highly selective to $H_2$, enabling Pd to be an excellent $H_2$ sensing material. In fact, most of the room-temperature solid-state $H_2$ sensors in a chemically variable environment use Pd metal and alloys as sensing elements.

Several fundamental problems are associated with bulk Pd-based hydrogen sensors. First, the diffusion of the hydrogen into bulk Pd such as a thick Pd film can result in an extraordinary large internal stress, leading to buckling of the films. This irreversible deformation leads to an irreversible resistance change. Secondly, the hydrogen atom diffusion in Pd is very slow at room temperature (the diffusion coefficient is $3.8\times10^{-7}$ $cm^2/s$ at 298 K). Thus, the long diffusion pathway of hydrogen into bulk Pd structures inevitably results in a long response time.

Intensive research has been conducted in recent years to develop a new generation of $H_2$ sensors with high speed, high sensitivity, miniature size and low cost.[6-36] Nanomaterials[7-31] have been a major focus in the search for high performance $H_2$ sensing elements due to their large surface area to volume (SA/V) ratios which could enhance the absorption/desorption rates of a chemical reaction and allow for shorter $H_2$ diffusion paths as well as confinement induced new properties. Among the various nanomaterials available, palladium (Pd) nanostructures[7,8,13,18,22-24,26,27] have shown very promising properties suitable for fast $H_2$ sensors.

Continuous Pd nanowires which respond to $H_2$ with an increase in resistance have been achieved through various nanofabrication techniques and have been systematically investigated.[8,9,22-24,26-27] Both experimental and simulation results show that their $H_2$ sensing ability increases and their response time decreases when the sensors' transverse dimensions shrink. The results clearly demonstrate that Pd nanowires can be excellent sensing elements for highly sensitive and fast acting $H_2$ sensors. The utilization of single palladium nanowires, however, faces challenges in nanofabrication, manipulation, and achieving ultrasmall transverse dimensions.

Scientists have developed/utilized various approaches to fabricate single Pd nanowires: (1) electrodepositing Pd at the step-edges on graphite; (2) electrodepositing Pd into nanochannels of porous membranes, for example anodic aluminum oxide, and (3) patterning Pd films via electron-beam (e-beam) lithography or deposition and etching under angles (DEA) methods. The last approach is costly because nano- (for example e-beam lithography tool) and microfabrication machines are expensive. It is difficult to achieve single nanowires with diameters smaller than 20 nm through these physical patterning techniques. In the first approach, it is inconvenient to reproducibly and massively fabricate single Pd nanowires by electrodepositing them on step-edges of graphite substrates. Furthermore, the nanowires grown on conducting graphite need to be relocated to an insulating substrate. Electrodepositing Pd into nanochannels of porous membranes is a convenient way to obtain large quantities of Pd nanowires. However, the problem with this method is making electrical contacts to individual nanowires, which typically requires the use of photo- or e-beam lithography and subsequent film deposition, resulting in a tedious fabrication process. Moreover, the surfaces of these nanowires can be contaminated during the process of dissolving the porous membranes to release the nanowires, degrading their gas sensing performance.

SUMMARY

In a first aspect, the present invention is a network of nanowires. The nanowires are metallic, each nanowire has a thickness of at most 20 nm, and each nanowire has a width of at most 20 nm.

In a second aspect, the present invention is a network of nanowires. The nanowires comprises Pd, each nanowire has a thickness of at most 20 nm, and each nanowire has a width of at most 20 nm.

In a third aspect, the present invention is a method of forming the network of nanowires, comprising forming a metallic layer on a substrate. The substrate may be, for example, an anodic aluminum oxide membrane filter.

In a fourth aspect, the present invention is a sensor, comprising the network of nanowires. The sensor may include nanowires comprising Pd, and the sensor may sense a change in hydrogen concentration from 0 to 100%. The sensor may include nanowires comprising Pd, and the nanowires may not form β-phase palladium hydride when exposed to hydrogen at room temperature.

In a fifth aspect, the present invention is a method of suppressing formation of β-phase palladium hydride, by forming a structure comprising palladium having a thickness of at most 4 nm.

In a sixth aspect, the present invention is an α-phase palladium hydrogen solid solution which is not a mixed phase of α-phase and β-phase palladium hydride, and which is not in the form of nanoclusters having an average particle diameter of 4 nm or less, wherein the hydrogen content of the solid solution is more than 0.015 atomic percent.

In a seventh aspect, the present invention is an electronic device comprising the network of nanowire. Example of the electronic device include a computer, a mobile phone, a vehicles, a fuel cell, a hydrogen storage tank, a facility for manufacturing steel, or a facility for refining petroleum products.

DEFINITIONS

The term "nano" means 100 nm or less. For example, a nanofilm is a film with a thickness of at most 100 nm; a nanowire means a wire with a thickness of at most 100 nm and a width of at most 100 nm; and a nanocluster means a cluster having a thickness of at most 100 nm, a width of at most 100 nm, and a depth of at most 100 nm. A nano-porous array or nano-porous network array is an array of pores, with each pore having a radius of at most 100 nm (that is, a diameter of at most 200 nm). In the case of pores which are not circular, the radius or diameter of the pore is the radius or diameter of a circle have the same area as the opening of the pore.

The term "Ultra-small" means 20 nm or less. Ultra small nanowires refer to nanowires with diameters less than 20 nm. In the case of the nanowires which are not circular, the diameter of the nanowire is the diameter of a circle having the same area as the cross-section of the nanowire.

An ordered array of pores means an array of pores showing order over a distance of at least 1 micrometer (1 μm or 1000 nm), in two dimensions. Any array of pores which is not ordered is a disordered array of pores. For example, the anodic aluminum oxide substrates illustrated in FIGS. 1a, 1b and 1c in Xiao et al., (ref. 45) are ordered arrays of pores. In contrast, the arrays of pores illustrated in FIGS. 1a, 1b and 1c of the present application are disordered arrays of pores.

The term nanowire is occasionally used for nanoclusters when describing experiments, however, all pure palladium nanowires formed on anodic aluminum oxide (AAO) having a thickness of 6.0 nm or less are nanoclusters. Furthermore, when a collection of structures is referred to as nanowires or nanoclusters, such as a network of nanowires, it means that the electrical conductivity properties of the structures collectively are dominated by those portions which are nanowires or nanoclusters, respectively.

A network of nanowires means a collection of nanowires interconnect at multiple points. The collection of nanowires includes at least 3 nanowires, preferably at least 10 nanowires, more preferably at least 100 nanowires, even more preferably at least 1000 nanowires, including 10 to $10^{10}$ nanowires, 100 to $10^8$ nanowires, and/or 1000 to $10^6$ nanowires. The network of nanowires includes at least 3 interconnections, preferably at least 10 interconnections, more preferably at least 100 interconnections, even more preferably at least 1000 interconnections, including 10 to $10^{10}$ interconnections, 100 to $10^8$ interconnections, and/or 1000 to $10^6$ interconnections. Each interconnection between nanowires may, independently of other interconnections, have a thickness, width and/or depth which is much greater than any of the nanowires in the network, including a thickness, width and/or depth which is great than 100 nm.

DETAILED DESCRIPTION

Figure 1:
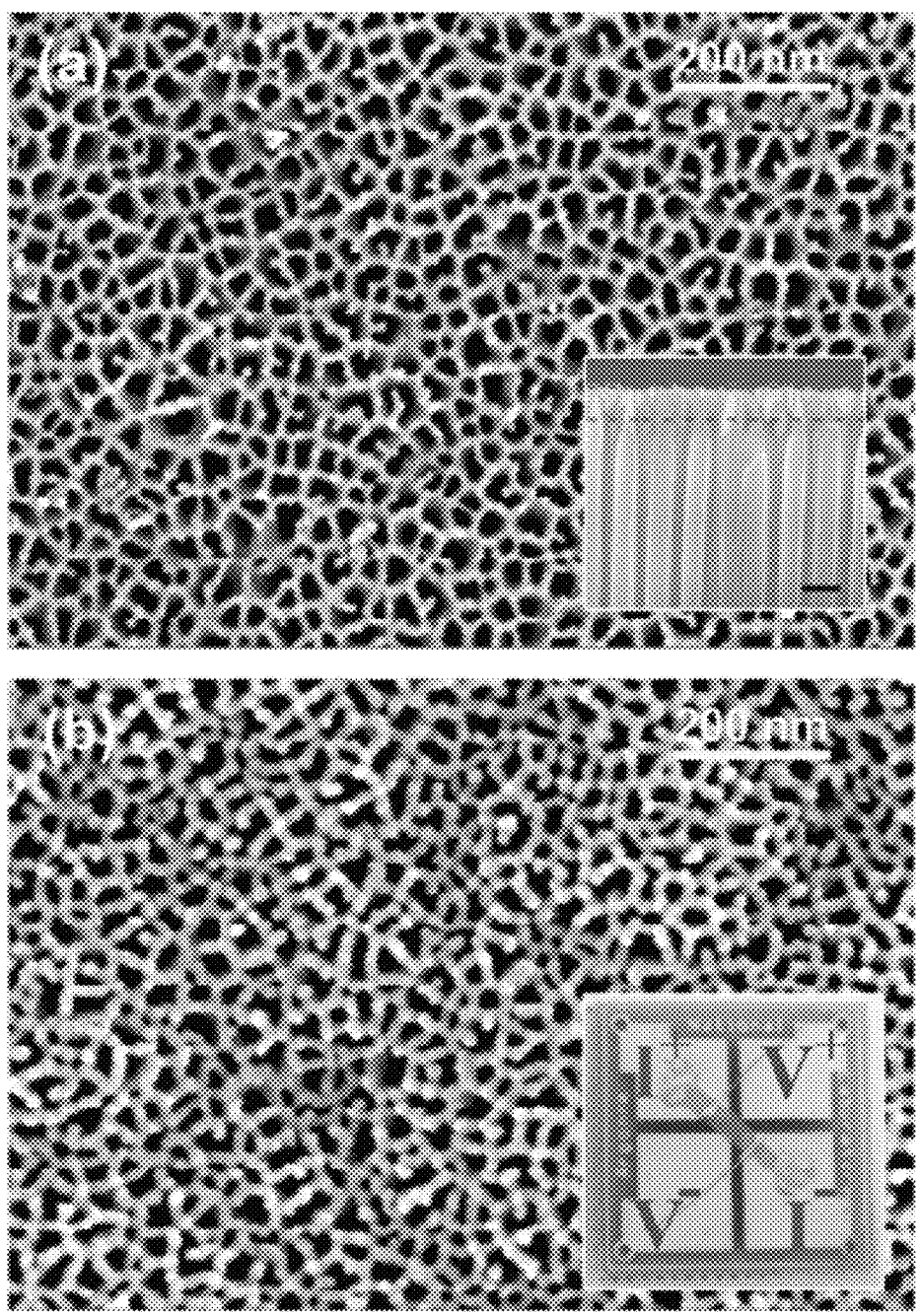
FIGS. 1a and 1b are scanning electron microscopy (SEM) micrographs of networks of Pd nanowires. The nominal thickness of the deposited Pd is 7 nm (a) and 30 nm (b), respectively. Inset to (a) is a cross section SEM micrograph of an Anodisc 13 membrane with filtration pore diameter of 20 nm. The part between the two dashed lines is the effective filtration layer. The black scale bar in the inset is 400 nm. Inset to (b) presents an optical image of a sample cut out from the Pd-coated membrane mounted on a sample holder.
FIG. 1c is a scanning electron microscopy (SEM) image of a 2 nm Pd/2 nm Cr nanowire network (Sample S1) coated on an Anodisc®13 alumina membrane with a nominal filtration pore diameter of 20 nm. The thicknesses of the deposited Pd and Cr layers are 2 nm each. The scale bar is 200 nm.

The present invention makes use of the discovery of a new fabrication method that allows for the formation nanowires and nanowire networks, by forming one or more layers on nano-porous arrays, such as anodic aluminum oxide substrates. These substrates are well known[41,46,72] and are commercially availble[66]. The nanowires formed have widths of 10 nm or less when formed on commercially available substrates.

The present invention also makes use of the discovery of nanowire networks formed of nanowires having a thickness of at most 20 nm and a width of at most 20 nm, and which preferably contain palladium (Pd). These networks of nanowires can be used to form hydrogen sensors, by electrically coupling them to a device suitable for measuring changes in resistance, such as an ohmmeter or an integrated circuit. More specifically, when the nanowires have a thickness of at most 4 nm, such as palladium nanowires formed on nanowires of chromium, preferably having a thickness of 1, 2, 3 or 4 nm, suppression of the β-phase of palladium hydride occurs, and such sensor can sense changes in hydrogen concentrations above 3%, for example from, or between, 0.01%, 100%, including 0.1% to 1%, 3%, 5%, 10%, 20%, 30%, 40%, 50%, 60%, 70%, 80% and 90%. Particularly interesting are hydrogen concentration ranging from, or between, 3%, 5%, 10%, 20%, 30%, 40%, 50%, 60%, 70%, 80%, 90% and 100%.

The present invention takes advantage of single palladium nanowires' high speed and sensitivity while eliminating the nanofabrication obstacles; high performance $H_2$ gas sensors are achieved by depositing pure palladium onto commercially available and inexpensive filtration membranes, or depositing a first layer of another material, such as chromium prior to deposition the palladium. This nanomanufacturing approach allows for the formation of Pd-nanowires based $H_2$ sensors for industrial applications.

There are several types of palladium compositions that can be used for the ultra small nanowires and nanoclusters. The palladium compositions can include, pure palladium (Pd), palladium alloy (for example, palladium-nickel (Pd—Ni), palladium-cerium (Pd—Ce)), palladium-other metals bilayers (for example, chromium/palladium (Cr/Pd), titanium/palladium (Ti/Pd) and molybdenum germanium/palladium (MoGe/Pd)), palladium/other metal multilayers (more than two-layers) (for example: gold/palladium (Au/Pd), nickel/palladium (Ni/Pd)), palladium/oxide bilayers and multilayers (for example, titania/palladium ($TiO_2$/Pd), zinc oxide/palladium (ZnO/Pd)), and palladium/metal hydride bilayers or multilayers (for example, gadolinium/palladium (GdHx/Pd), magnesium hydride/palladium (MgHx/Pd)).

One, 2, 3, 4, 5, 6, 7, 8 or more layers may be formed, with each layer preferably comprising a metal, for example Mg, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Al, Ga, In, Si, Ge, Sn, Pb, Sb, Bi, a Lanthanide series metal, an actinide series metal, alloys thereof and compounds thereof. Preferably the top layer which is exposed to ambient atmosphere contains palladium. However, for sensing gases other than hydrogen, a different metal or metallic material could be used as the top layer. For example hydrogen sulfide ($H_2S$) could be sensed using a layer or top layer of silver (Ag) or oxygen could be sensed using a layer or top layer of aluminum (Al). If the thickness of the layer is 20, 19, 18, 17, 16, 15, 14, 13, 12, 11, 10, 9, 8, 7, 6, 5, 4, 3, 2 or 1 nm, then reaction with such gases would affect the conductivity of the layer. In the case of palladium having a thickness of 20, 19, 18, 17, 16, 15, 14, 13, 12, 11, 10, 9, 8, 7, 6, 5, 4, 3, 2 or 1 nm, the reaction with hydrogen is reversible, allowing for reuse of the sensors. As long as the nanowires or nanoclusters are metallic, then changes in resistivity may be measured, either an increase, decrease or more complex combinations of increases and decreases. Calibration may be carried by using a test sensor and know concentrations of analyte. In the case of nanoclusters, a change in size may be sufficient to provide a change in resistivity as the contact or tunneling of electrons between clusters change as they swell or contract from chemical reaction, alloying, or the formation of solid solutions.

The nanowires can be used as-prepared or annealed at high temperatures up to 800 degrees Celsius in various gas environments. The thickness and width of the ultra-small palladium-based nanowires and nanoclusters are preferably from 1 to 20 nanometers. The response times of the Pd nanowire networks decrease with shrinking thickness and width and are much shorter than those of continuous films of the same thickness. The hydrogen responses of these sensing networks are from the continuous nanowires and discontinuous nanocluster chains at thicknesses above and below 4.5 nm or 6 nm, respectively. These networks have the advantages of individual nanowires and nanocluster chains but reduce the fabrication cost. At room temperature the hydrogen response time of these networks can be as low as hundreds of milliseconds.

Furthermore, in the case of continuous Pd nanowires having a thickness below 4.5 nm, the suppression of the β-phase of palladium hydride occurs, extending the range of the sensor beyond 3% hydrogen all the way to 100% hydrogen.

In one aspect, the present invention provides for a method of making the hydrogen sensors by depositing desired palladium compositions on porous substrates with widths of the sections between holes less than 20 nm, and creating nanowire networks. These porous substrates can preferably be commercially available filtration membranes, or the porous substrates can be manufactured as desired.

Porous ANODISC® inorganic membranes from Whatman have been widely used as filters in chemistry. The straight nanochannels in the bulk of the membranes have also been utilized as templates to grow nanowires and nanotubes. Though the available nominal effective filtration pore diameters are 20 nm, 50 nm, 100 nm, and 200 nm, on the surface, the diameter of the nanochannels in the bulk of the membrane is unchanged (that is, 200 nm). The effective filtration is determined by the pore diameters of a very thin (~100-200 nm) layer of a nano-porous network array supported on top of a 60 μm thick membrane containing vertical nanochannels of 200 nm in diameter (shown in FIGS. 1a, 1b and 1c). For example, for a nominal effective filtration pore diameter of 20 nm, the material sections between neighboring pores is less than 10 nm wide. These sections are utilized as a template to form a wire network array of Pd by depositing Pd onto it. The commercial ANODISC® can be further etched with appropriate acid (for example, phosphoric acid) to shrink the width of the section between neighboring pores.

The deposition of the palladium composition can be performed with any thin-film deposition technique known in the art, for example, sputtering, thermal evaporation, or electron-beam evaporation.

In another aspect, the present invention further provides for a method of detecting hydrogen, by exposing the hydrogen sensor as described above to an environment, changing the resistivity of the hydrogen sensor, and detecting the presence of hydrogen. If the environment includes hydrogen, the hydrogen sensor will detect it. As described above, the resistivity of the palladium nanowire hydrogen sensor changes based on the presence of hydrogen in the environment. The hydrogen sensor can transmit the amount of hydrogen detected to a display if desired to a user, this information can be stored in a computer processor, or transmitted to a computer to perform a certain operation upon the detection of hydrogen. The hydrogen sensor has a response time as short as hundreds of milliseconds, a great improvement over the response time of the previous sensors.

The hydrogen sensor of the present invention can be used in applications such as, safety sensors in hydrogen powered cars, Lead (Pb) acid batteries, personnel monitors and other places where hydrogen is present and requires detection.

The hydrogen sensor of the present invention has several advantages over the prior sensors. The ultra-small (20 nm or less) thicknesses and widths of the nanowires which form the network reduce the hydrogen diffusion time and increase the surface area to volume ratio, resulting in a short response time of the sensor. Any thin-film deposition technique can be used to deposit the Pd and other desired Pd compositions for forming the nanowire networks which have the advantage of single nanowires, leading to cost-effective fabrication of the sensor. The sensor is more reliable because it consists of many conducting paths in parallel. Thus, the hydrogen sensor of the present invention is a high speed sensor that is able to work at room temperature, is inexpensive and also can be small size and low power consumption.

After formation, the substrate may be removed to form free-standing films. In the case of aluminum oxide substrates, the substrate may be dissolved using acids such as phosphoric acid, or alkaline materials such as aqueous sodium hydroxide. A polymer may be polymerized on the top of the films to provide support during a dissolution process.

Preferably, anodic aluminum oxide substrates are used. The substrates may have ordered or disordered arrays of nanopores; the anodic aluminum oxide substrates illustrated in FIGS. 1a, 1b and 1c in Xiao et al. (ref. 45) are ordered arrays of pores (which, however, have an oxide width of 50 to 60 nm between each pore). Commercially available nominal effective filtration pore diameters of 20 nm, 50 nm, 100 nm, and 200 nm are available. Furthermore, Xiao et al., (ref. 41) and Xiao et al., (ref. 45) describe how to form further variations on the commercially available structures.

The network of nanowires of the present invention may be incorporated into a semiconductor device such as an integrated circuit, a programmable logic device, a data communications device; etc. where is may act as a sensor for hydrogen or other gases. Furthermore, a network of nanowires or any of these semiconductor devices may be incorporated in an electronic device, for example a computer, mobile phone, a vehicles such as an airplane or an automobile, a fuel cell, a hydrogen storage tank or facility, a facility for manufacturing glass or steel, or a facility for refining petroleum products.

EXAMPLES

Example 1

Palladium Nanowires, Nanowire Networks and Nanoclusters Formed Directly on Substrates, and Hydrogen Sensors Formed from Palladium Nanowires, Nanowire Networks and Nanoclusters Formed Directly on Substrates ANODISC® 13 membranes with nominal filtration pore diameter of 20 nm were purchased from Whatman Company.

They were cleaned with acetone in an ultrasonic bath for 10 minutes and rinsed with de-ionized water followed by ethanol and dried with high purity nitrogen gas. With the filtration layer facing the Pd target, Pd was deposited onto the membrane using an AJA ATC-2400 sputtering system with a base vacuum of ~1×10$^{-7}$ Torr. Argon was used as the working gas at a pressure of 3 mTorr. The deposition rate was 1.3 Å/s. To check the morphology of the deposited Pd, the final product was imaged with a high-resolution field emission scanning electron microscope (SEM) (Hitachi S-4700 II). A homemade hydrogen sensor testing system using a series of ultrafast solenoid valves and a minimized dead volume of the gas passages was used to accurately characterize these sensors with response times down to tens of milliseconds.

FIGS. 1a and 1b present top-view SEM micrographs of ANODISC® 13 membranes with pore diameter of 20 nm after deposited Pd with nominal thicknesses of 7 nm and 30 nm, respectively. The morphology of the membrane does not change significantly after coating with 7 nm thick Pd (FIG. 1a). With increasing thickness of the deposited Pd, however, the pores shrink and the widths of the Pd sections between neighboring pores become larger, as can be seen from the micrograph presented in FIG. 1b. Quantitatively, the widths of the Pd nanowires (that is, sections between the pores) in FIGS. 1a and 1b are 7-9 nm and 12-15 nm, respectively. Though detailed investigations were not carried out on the relationship between the width of the Pd nanowires and the nominal thickness of the deposited Pd, it is reasonable to estimate that their widths are close to the widths of the sections between pores in the bare templates and their thickness is that of the deposited Pd if its nominal thickness is less than 10 nm. This relation is more complicated with thicker deposited Pd. It was found that wire networks with deposited Pd less than 10 nm are more desirable as sensors. Those with thicker deposited Pd were also studied for comparison.

Figure 2:
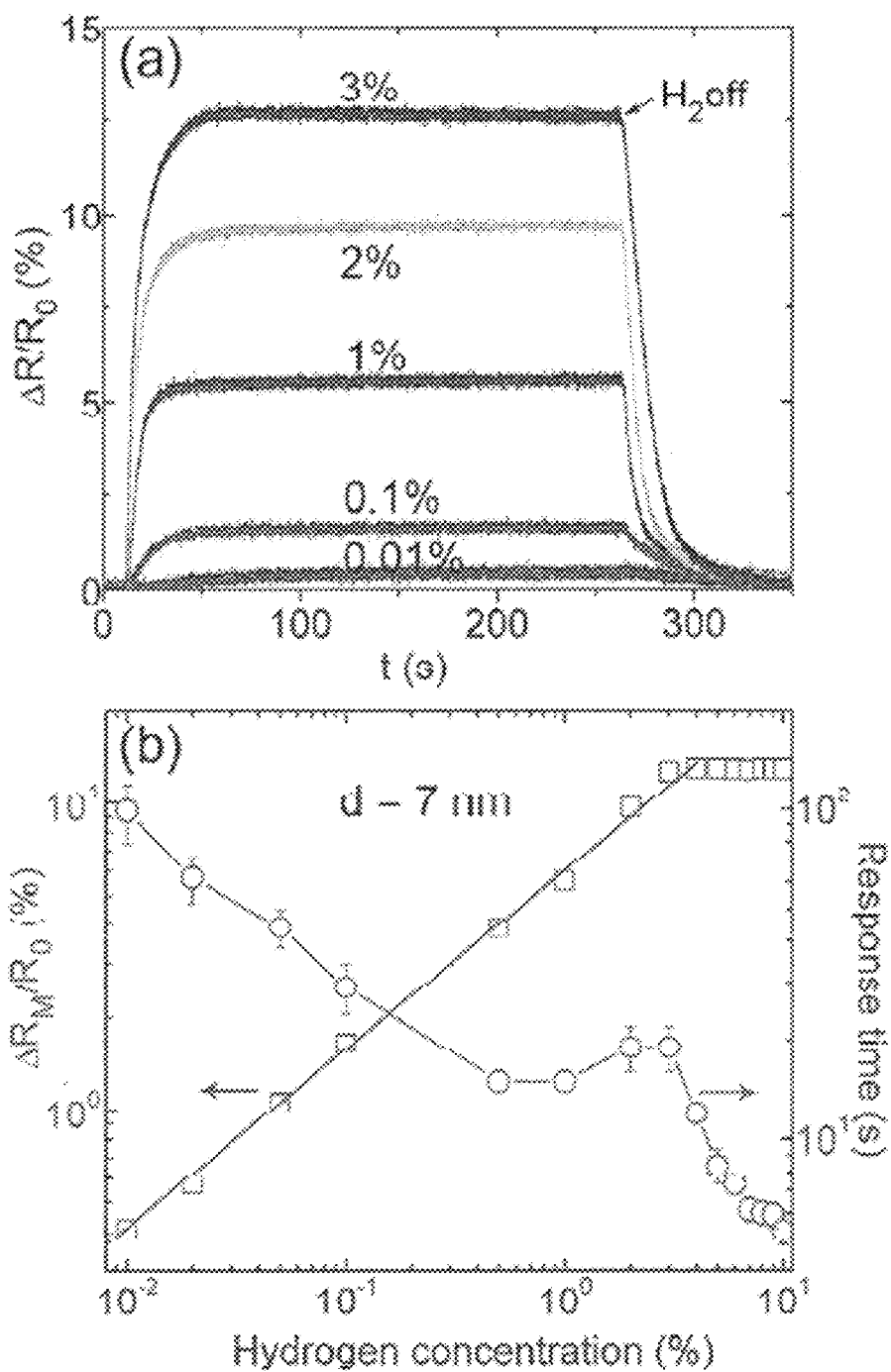
FIGS. 2a and 2b show $H_2$ response of a 7 nm thick Pd nanowire network: (a) resistance changes $\Delta R/R_0$ with time at various concentrations, resistance data of 10 seconds prior to $H_2$ entering the testing chamber were taken as the baseline, and (b) concentration dependences of the maximal resistance change $\Delta R_M/R_0$ and response time. $R_0$ is the resistance in the absence of hydrogen gas and $\Delta R$ is defined as the absolute resistance change $R(t)-R_0$ and $\Delta R_M$ is the maximal resistance change at a specific concentration, the response time is defined as the rise time to reach 90% of its maximal change, i.e. $\Delta R/\Delta R_M=0.9$, and the solid line is a power-law fit with an exponent of 0.58.
Figure 3:
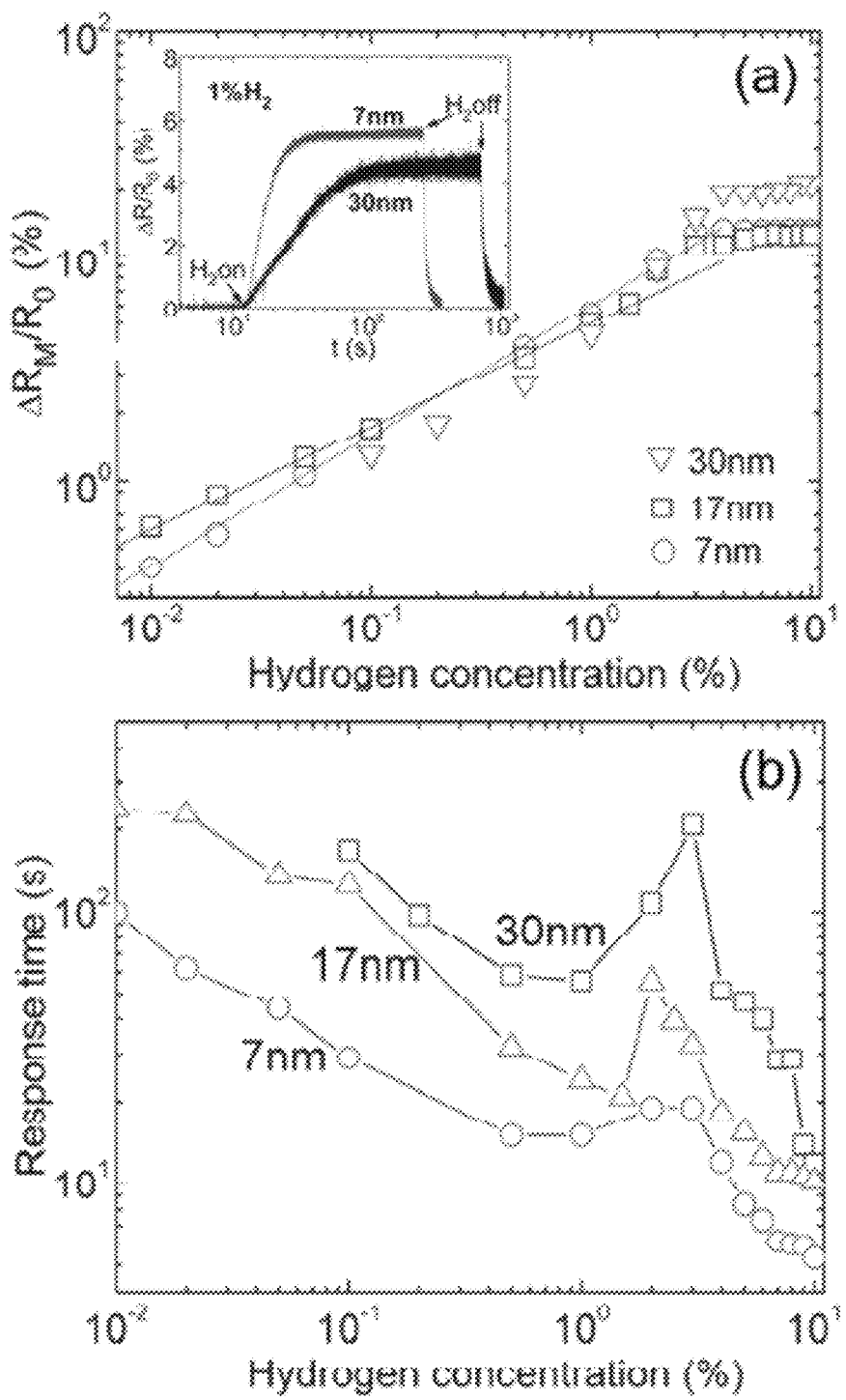
FIGS. 3a and 3b show comparisons of the hydrogen responses of Pd nanowire networks (NW) and their reference films: (a) resistance changes $\Delta R/R_0$ with time at $H_2$ concentrations of 0.1% and 1%, and (b) Concentration dependences of the response times, the nominal thicknesses of the deposited Pd are given in the figures.

A plot of the time dependence of the relative resistance change $\Delta R/R_0$ for a 7 nm thick Pd nanowire network at various $H_2$ concentrations is shown in FIG. 2a. In the presence of hydrogen gas, the resistance of the sample increases with time and saturates at a value that depends on the gas concentration. FIG. 2b demonstrates the concentration dependence of the maximal resistance change $\Delta R_M/R_0$ and the response time. The results are similar to those reported for electrodeposited nanowires where $\Delta R_M/R_0$ first increases with $H_2$ concentration up to about 3% and then remains constant at higher concentrations. Furthermore, quantitative analysis demonstrates that the concentration dependence of the maximal resistance change follows a power-law relation with an exponent of 0.58 for concentrations up to 3%. This indicates that the interaction of $H_2$ and Pd in this concentration range follows Sievert's law. That is, the ratio of the dissolved atomic hydrogen to Pd atoms can be described to a good approximation with a power-law dependence of the hydrogen partial pressure (that is, $H_2$ gas concentrations in the experiments) and the change of this ratio leads to a proportional $\Delta R_M/R_0$ response. The exponent of 0.58 is slightly larger than those (~0.4-0.50) reported in the literature for Pd films. However, as shown in FIG. 3a, the exponent decreases when the transverse dimensions (thickness, width or both) of the Pd nanowires are increased. For example, an exponent of 0.46 is obtained for the 30 nm thick Pd nanowire network. Since a larger power-law exponent corresponds to a faster change in resistance with changing $H_2$ concentration, this shows that sensors with smaller transverse dimensions have better resolutions. This is reasonable because the surface to volume ratio is larger in Pd nanowires with smaller transverse dimensions and the surface can have denser atomic hydrogen sites than the bulk.

The $\Delta R_M/R_0$ saturation at a $H_2$ concentration of 3% is related to the transition from α-phase to β-phase of the Pd/H system. The resistance in the mixed phase of the α-phase and β-phase is not sensitive to the change in $H_2$ concentration. This transition has also significant effect on the response time. As presented in FIG. 2b for the 7 nm thick Pd nanowire network, the response time at low $H_2$ concentrations becomes shorter when more $H_2$ is present. However, the sample needs longer time to reach its steady state at $H_2$ concentrations of 1-3% than that at 0.5%, resulting in a bump in the response time versus concentration curve. Both the response time and its concentration dependence are quantitatively comparable to those of the smallest electrodeposited single Pd nanowire where the small bump was attributed to the α- to β-phase transition. This bump evolves into a peak with increasing transverse dimensions, as shown in FIG. 3b for the Pd nanowire networks with nominal thickness of 17 nm and 30 nm for the deposited Pd. As expected, FIG. 3b also shows that the response time becomes longer at all $H_2$ concentrations for samples with thicker Pd nanowires.

Figure 4:
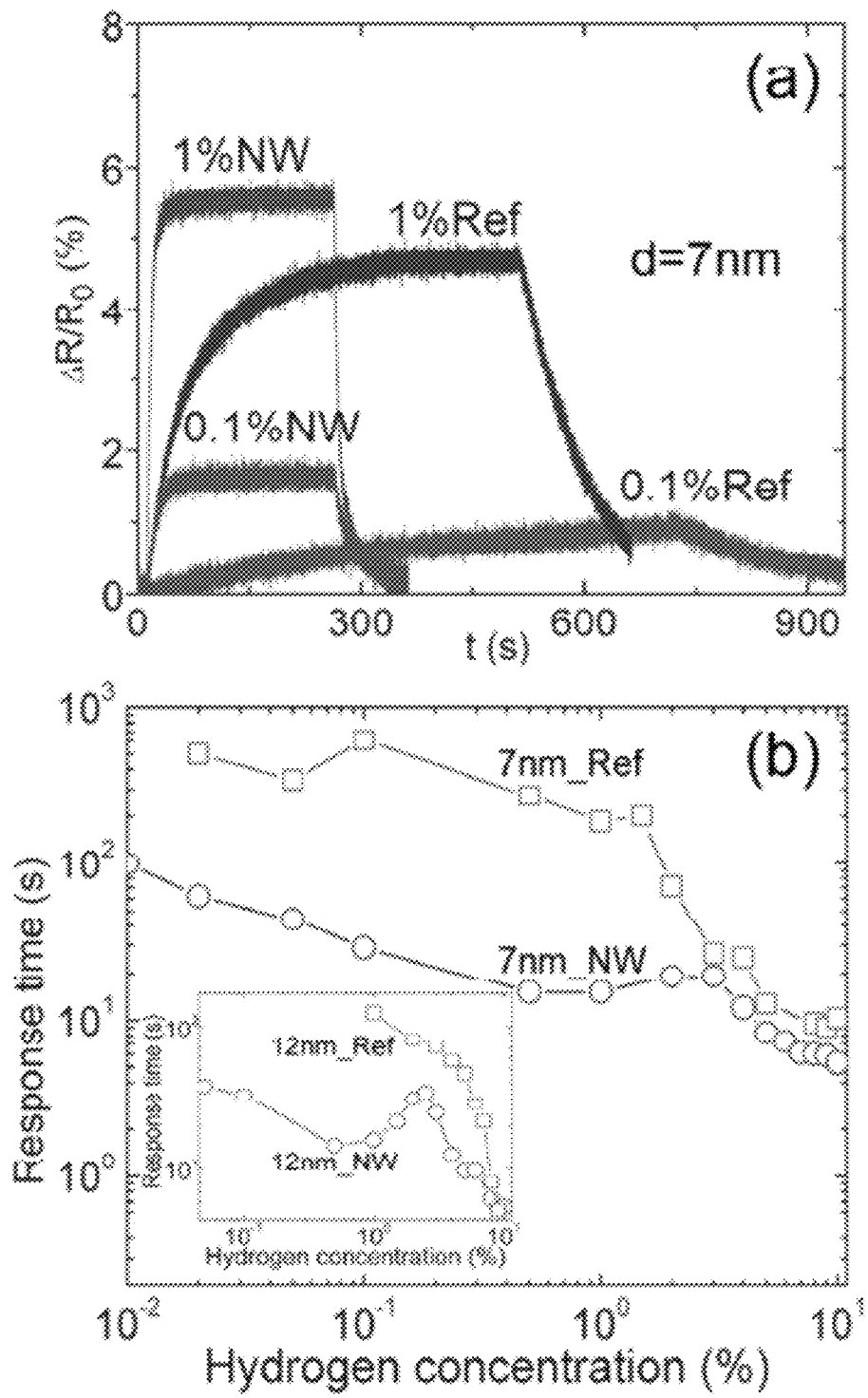
FIGS. 4a and 4b show comparisons of the hydrogen responses of Pd nanowire networks with various nominal thicknesses of the deposited Pd: (a) and (b) present $H_2$ concentration dependences of the resistance changes $\Delta R_M/R_0$ and response times, respectively, the solid lines to fit the data of the 7 nm and 30 nm thick Pd nanowire networks represent a power-law exponents of 0.58 and 0.46, respectively.

Lee et al. found that the buckling and hysteresis behaviors observed in thick (d>20 nm) Pd films do not appear in continuous ultra-thin films (d=5 nm). Since a thickness of a few nanometers is so small, one might think the response time of such a ultra-thin Pd film to $H_2$ gas could be very short and it might be close to that of a ultra-thin nanowire. If this were the case, $H_2$ sensors based on ultra-thin Pd films would be preferable since it is more convenient to fabricate ultra-thin films than ultra-thin nanowires. Thus, it is necessary to compare the $H_2$ responses of ultra-thin Pd films and our network of ultra-thin Pd nanowires. In experiments, a Si substrate (with a $SiO_2$ layer of 100 nm thick) was placed near the ANODISC® 13 membrane and Pd was deposited onto them simultaneously, ensuring the same thickness for both the Si substrate reference film sample and the ANODISC® substrate sample. FIG. 4a presents the evolution of the resistance change for the 7 nm thick network of Pd nanowires and its reference film at $H_2$ concentrations of 0.1% and 1%. It is evident that the reference film requires a much longer time to reach its steady state. As shown in FIG. 4b and in its inset, for the 7 nm and 12 nm thick samples, the response times of the reference films were almost one order of magnitude longer than those of the nanowire networks at $H_2$ concentrations below 1%, though the difference becomes smaller at high $H_2$ concentrations, that is, in the β-phase. The results clearly demonstrate that even for a Pd object with dimensions down to a few nanometers, $H_2$ diffusion from the sides and the surface to volume ratio still plays a critical role on the $H_2$ response time.

Figure 5:
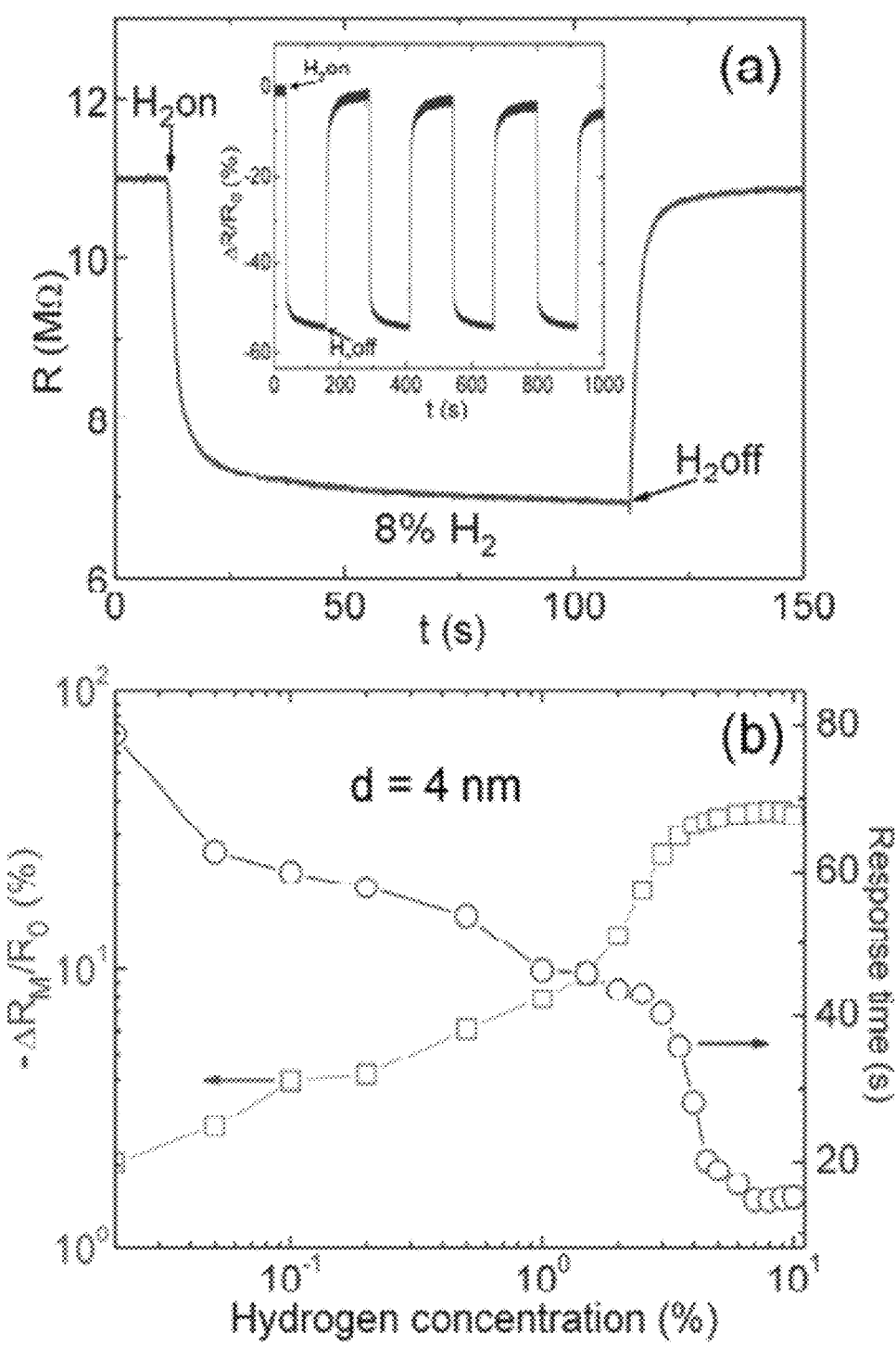
FIGS. 5a and 5b show $H_2$ response of a 4 nm thick Pd nanowire network: resistance change $\Delta R/R_0$ with time at $H_2$ concentration of 8%, inset shows data with more cycles for a sample made from different part of the same membrane, and concentration dependences of the maximal resistance change $\Delta R_M/R_0$ and response time.

The above results directly show that networks of Pd nanowires with even smaller transverse dimensions need to be pursued. Since the width of the Pd nanowires is close to that of the template (the width of the sections between neighboring pores in the ANODISC® 13 membrane) which is fixed, their thickness was reduced by depositing less Pd. Experimentally, samples were examined with Pd thickness down to 2 nm with a thickness interval of 0.5 nm. The samples with thickness less that 3.5 nm have resistance >100 MΩ) over the input impedance of our electronic circuit. A typical time dependence of the resistance for a 4 nm thick network of Pd nanowires in the presence of hydrogen gas is presented in FIG. 5a. Differing from the data shown in FIGS. 2a, 3a and 4a, this sample became more conductive upon $H_2$ exposure. This behavior is very similar to that observed in fractured single Pd nanowires where the decrease of resistance is attributed to the disappearance of gaps due to the dilation of the Pd after absorbing hydrogen. This means that when the thickness of the coated Pd layer is extremely thin (for example, 4 nm or less), the Pd nanowires forming the network become discontinuous. As shown by the concentration dependence of the resistance change $\Delta R_M/R_0$ presented in FIG. 5b, however, the sample can detect hydrogen at concentration levels down to 0.01% while the resistance of the fractured electrodeposited Pd nanowires changes only at a $H_2$ concentration of 1% or higher.

This difference can be understood in terms of physical gap sizes: the gaps in electrodeposited nanowires are tens of nanometers or larger. The significant volume increase of the β-phase that occurs at $H_2$ concentrations of 1% or higher is needed to make them closed. On the other hand, the gaps in the sample are very small and electrons can tunnel through them. Any slight volume change due to the hydrogen-induced palladium lattice expansion can make the gap smaller, leading to better electron tunneling and hence to a resistance decrease. In fact, both the capability to detect $H_2$ at low concentrations and the resistance change $\Delta R/R_0$ of this 4 nm thick network of Pd nanowires are comparable to those of the two-dimensional (2D) Pd nanocluster array formed on a glass substrate covered with a self-assembled monolayer (SAM). The latter has gaps of a few nanometers between neighboring nanoclusters and electron tunneling dominates the electric properties at low $H_2$ concentrations. As shown by the response time at various $H_2$ concentrations given in FIG. 5b, however, the 4 nm thick network of Pd nanowires is much slower than the SAM promoted 2D Pd nanocluser array in response to $H_2$ exposure. This highlights the importance of SAM induced reduction of the stiction between the palladium and the substrate to the response time of the sensor. The strong adhesion of Pd on the substrate may also prevent some of the Pd atoms to return to their original locations, resulting in an decrease of the amplitude of the resistance change with increasing cycles as that shown in the inset of FIG. 5a. Though siloxane was successfully used to achieve SAMs on glass substrates, efforts are needed to find appropriate molecules to form SAMs on the Anodisc® filtration membranes.

Figure 6:
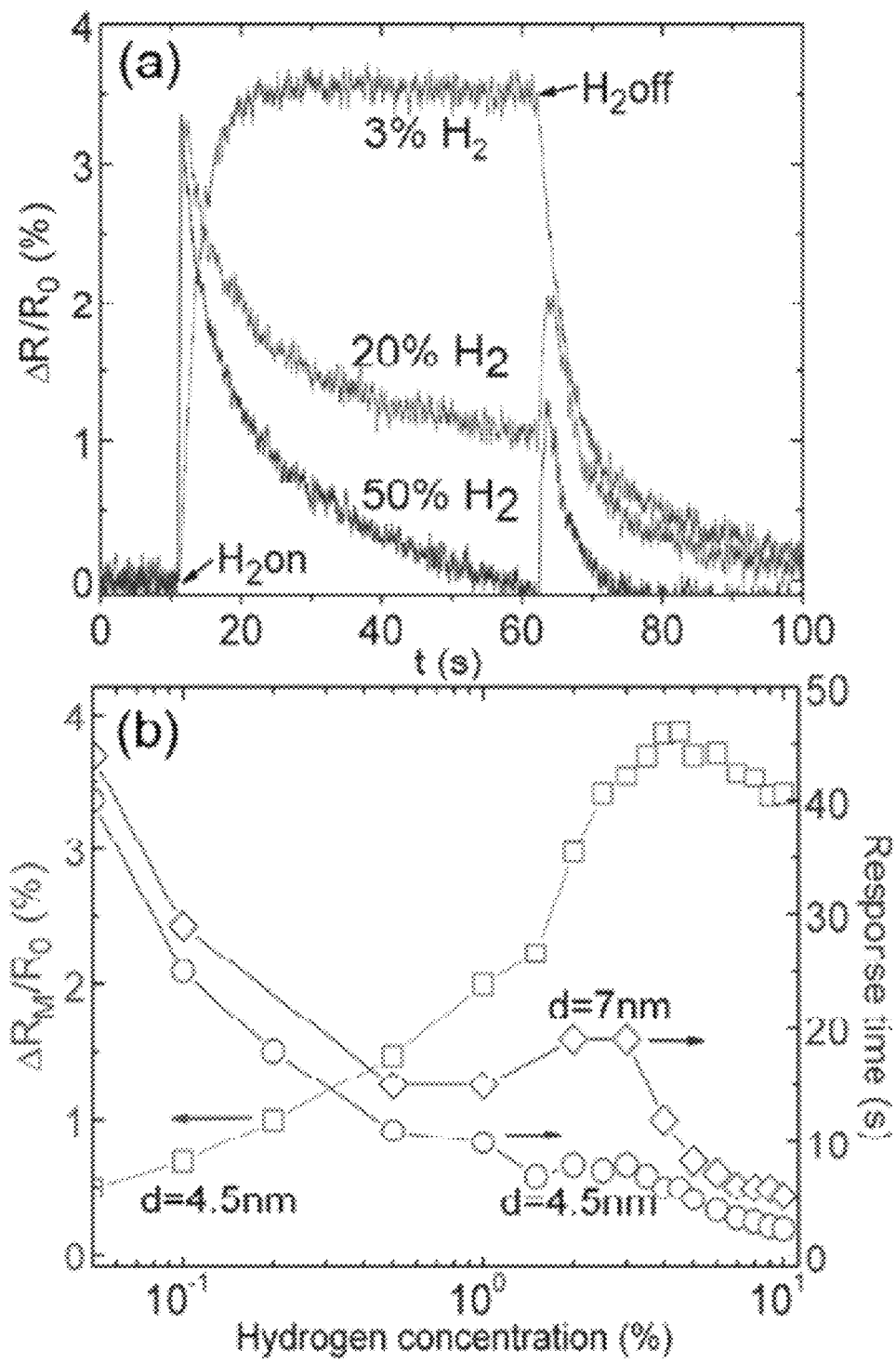
FIG. 6 shows $H_2$ response of a 4.5 nm thick Pd nanowire network: (a) resistance changes $\Delta R/R_0$ with time at various concentrations. (b) Concentration dependences of the maximal resistance change $\Delta R_M/R_0$ and response time. The response times of the 7 nm thick sample at various concentrations were also replotted in (b) for comparison.

Theoretically, one gap in a single nanowire causes it to be discontinuous and non conductive. For a network of nanowires, however, gaps in some of the nanowires can only increase the resistance of the network rather than make it non-conductive because electrons can always flow through the conducting pathways as long as the number of the broken nanowires is below the percolation threshold. This implies that the transition or a crossover from a network without a significant number of broken nanowires to that consisting of mainly broken nanowires should be second order. The data in FIG. 2 show that the number of broken Pd nanowires in the 7 nm thick network is negligible and that its $H_2$ sensing mechanism is based on the resistance change of the nanowires upon $H_2$ exposure. Meanwhile, FIG. 5 indicates that broken Pd nanowires dominate the electric transport of the 4 nm thick network and its $H_2$ sensing mechanism is based on a resistance decrease due to the $H_2$ induced closure of gaps. Networks with thicknesses between 4 nm and 7 nm may have a large number of broken Pd nanowires while there are also many flow pathways for electrons through continuous nanowires. That is, the mentioned two sensing mechanisms may compete in some networks where the thicknesses range from 4 nm to 7 nm. In fact, such a behavior does occur in a 4.5 nm thick network. As presented in FIG. 6a, the resistance versus time curves for $H_2$ concentrations of 20% and 50% have two peaks just after the $H_2$ is turned on and off. The first peak corresponds to the fast resistance increase from the through-pathways of continuous Pd nanowires upon $H_2$ exposure, followed by the closure of gaps in the broken nanowires which leads to an opposite resistance decrease. On the other hand, the resistance increase at the second peak when $H_2$ is turned off is due to the gap re-opening in the previous broken nanowires while the decay is due to the release of $H_2$ from the continuous Pd nanowires. FIG. 6a also indicates that high $H_2$ concentrations are needed to observe both of the sensing mechanisms in the same sample. This is because newly formed electron flow-pathways from the broken nanowires due to the $H_2$ induced gap closure are in parallel to those of the existing continuous nanowires. Furthermore, there are gaps of various sizes in broken nanowires and one gap can destroy an electron flow-pathway. Higher $H_2$ concentration can induce larger expansion of the Pd lattice thus decreasing the density of gaps so that more new flow-pathways can be formed. At low $H_2$ concentration, the resistance change induced by the gap-closure in some broken nanowires cannot change the total resistance significantly. Thus the sample can reach a steady state, as shown by the curve obtained at $H_2$ concentration of 3%. By comparing the responses of the 7 nm and 4.5 nm networks to 3% $H_2$ as given in FIG. 2a and FIG. 6a, it was found that the resistance change $\Delta R_M/R_0$ in the latter is a factor of ~4 smaller. In fact, as shown in FIG. 6b, the $\Delta R_M/R_0$ of the 4.5 nm thick networks are smaller than those of the 7 nm thick network at all the measured $H_2$ concentrations. This is simply because that the latter has more parallel through-pathways of the continuous nanowires that contribute to the total resistance change upon $H_2$ exposure.

A comparison of the $H_2$ response times given in FIG. 2b and FIG. 6b reveals that the speed of the 4.5 nm thick network is double that of the 7 nm one. This indicates that the response time can be further shortened if even thinner continuous nanowires can be fabricated. However, a Pd film fabricated with convenient deposition methods such as sputtering and thermal evaporation will have a percolation threshold of 3.5-5.0 nm. Thus, the values presented in FIG. 6b may be not far away from the shortest response times that can experimentally be achieved in continuous Pd nanowires, unless other more advanced deposition methods, for example, molecular beam epitaxy (MBE) is used to grow even smaller nanowires. Similar to that observed in single pure Pd nanowires and thin films, the resistance change $\Delta R_M/R_0$ of our networks of Pd nanowires saturates at $H_2$ concentrations higher than 3%. This can seriously hinder the applications of sensors based on such networks. As demonstrated by the disappearance of the $\Delta R_M/R_0$ saturation in the $H_2$ response of Pd/Ni alloy films, however, such a limitation in our Pd nanowire networks could be eliminated by replacing the pure Pd with Pd alloys. In fact, pure Pd was chosen to fabricate the networks simply because data on single Pd nanowires are available for comparisons.

In summary, a new type of hydrogen sensor was achieved based on networks of ultra-small (<20 nm) palladium nanowires formed on commercially available filtration membranes. The sensors have high sensitivity and short response times. The approach of the present invention can also provide a general way to utilize the improved performance or new properties of single nanowires of pure Pd, Pd alloy and other hydrogen sensing materials while eliminates the nanofabrication obstacles.

Example 2

Palladium/Chromium Nanowires, and Nanowire Networks, and Hydrogen Sensors Formed from Palladium/Chromium Nanowires, and Nanowire Networks Previous results have shown that the response of the Pd nanowire network sensors become faster when the thickness of the network is reduced.[37] However, a crossover from continuous to broken nanowire networks occurs at a certain critical thickness, similarly to what has been observed in ultrathin Pd films,[1,13] limiting the potential for further decreasing the response time through reduction of the network thickness. These newly developed Pd nanowire network sensors also inherit the drawback of the single Pd nanowire: an inability to distinguish $H_2$ concentrations above 3%. This deficiency of the sensor definitely hinders its potential applications, for example, in a fuel processor and as a safety monitor in a vehicle which require the device to be sensitive to hydrogen in the range 1-100% and 0.1-10%, respectively.[38] Here we report experiments aiming to further improve the performance of this type of $H_2$ sensor by reducing the thickness of the network while enabling the Pd nanowires to be continuous. By first depositing a layer of chromium (Cr) with thickness of 1 nm-3 nm onto the filtration membrane substrate, we create networks of Pd/Cr nanowires with the thickness of the continuous palladium layer as low as 2 nm. These Pd/Cr nanowire networks are faster than the pure palladium counterparts in responding to $H_2$ gas. The excellent adhesion of Cr to the substrate also helps to significantly improve the durability of the sensor. Even more importantly, the Pd/Cr sensors are able to distinguish $H_2$ concentrations up to 100%, eliminating a crucial drawback of its pure palladium counterparts. Since this change can be attributed to the confinement-induced suppression of a phase transition in the Pd/H system, our results demonstrate that the performance of $H_2$ sensors based on Pd nanostructures can indeed go beyond the benefits expected from the increased SA/V ratios and shorter diffusion distances.

When a metal is deposited onto a non-metallic substrate, it initially tends to nucleate into fine particles. The morphology of the particles is governed by the minimization of the surface free energy.[39,40] Using the equilibrium of surface tension, one can write: $\gamma_{sg} = \gamma_{ms} + \gamma_{mg} \cos\theta$, where $\theta$ is the contact angle between the particle and the substrate, $\gamma$ is the surface or interfacial energy, and the subscripts s, m, and g stand for substrate, metal particle, and gas, respectively. If the metal-substrate interfacial energy $\gamma_{ms}$ is smaller than the surface energy of the substrate $\gamma_{sg}$, $\theta$ will be smaller than 90°. In this case the supported particle will tend to have a half-dome shape or even spread over to have a raft-like morphology. If $\gamma_{sg}$ is smaller than $\gamma_{ms}$, then $\theta$ will be greater than 90°, and the particles tend to appear spherical or polyhedral. In the latter case, the layer of metal must reach a $\theta$ dependent critical thickness to form a continuous film on the substrate. A crossover from continuous to discontinuous behavior was observed in Pd films on $Si_3N_4$ and $SiO_2$ substrates at thicknesses of 4 nm and 5 nm, respectively.[1,13]

Porous Anodisc® filtration membranes from Whatman®—the substrates used to form Pd nanowire networks—are made of anodic aluminum oxide.[37,41] It is well known that $Pd/Al_2O_3$ system has weak metal-substrate interaction.[39,40] Thus, a Pd layer on an alumina substrate may be continuous only when it achieves critical thickness. Indeed, the $H_2$ response of this newly developed pure Pd nanowire network sensor depends strongly on the thickness of the Pd layer:[37] at 7 nm and thicker, the network consisting of continuous Pd nanowires has a shorter response time when its thickness is reduced. At 4 nm and below, the majority of the Pd nanowires become discontinuous and the $H_2$ induced resistance changes of the network are dominated by broken Pd nanowires, leading to a retarded $H_2$ response. We also found coexistence of continuous and broken Pd nanowires at thicknesses of 4 nm<d<7 nm where resistance changes contributed from broken and continuous Pd nanowires compete, which is consistent with observations on ultrathin Pd films on polymer (SU8) substrates.[29]

Crispin et al. found that the contact angle between Ni and alumina can be significantly reduced by adding a small amount of chromium (Cr). For example, the contact angle is close to 90° on both sapphire and polycrystalline alumina with 10% Cr in Ni and is ~75° with 20% Cr.[42,43] Here we demonstrate that an addition of a Cr buffer layer as thin as 1 nm between Pd and alumina substrates (Anodisc® filtration membranes) can modify the Pd-substrate interaction and reduce the critical thickness of the Pd layer required to form a continuous Pd layer. We were able to achieve networks of continuous Pd nanowires with thicknesses down to 2 nm on Anodisc® filtration membranes.

Figure 1C:
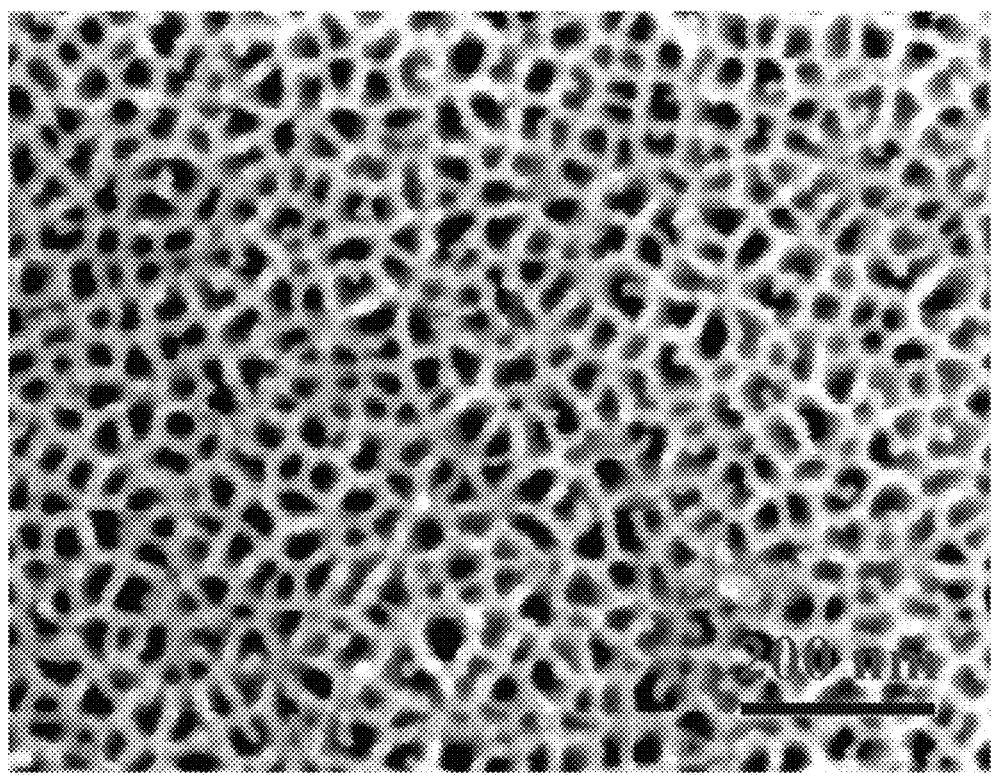

FIG. 1c presents a typical top-view scanning electron microscopy (SEM) micrograph of a Pd/Cr nanowire network (Sample S1) deposited onto an Anodisc®13 membrane with an effective filtration pore diameter of 20 nm. The image was taken of a Pd/Cr sample with a nominal thickness of 2 nm for both the deposited Pd and Cr. As listed in Table I, we conducted experiments on Pd/Cr nanowire network samples (Sample S1-S9) with thickness ranging from 1 nm to 3 nm for the Cr layer and from 2 nm to 7 nm for the Pd layer with a thickness step of 1 nm. Since the deposited Pd/Cr layer is thin (<10 nm), the morphology of the network simply duplicates that of the bare filtration membrane.[37,40] The widths of the Pd/Cr nanowires (i.e. sections between the pores) in FIG. 1c are 7-9 nm. A cross-section SEM imaging finds no metal inside the pores, consistent with those reported in networks of pure Pd nanowires on filtration membranes[37] and in other perforated films sputter-deposited on nanoporous alumina substrates.[44,45]

TABLE I

Baseline Resistances ($R_0$) of the Pd/Cr Nanowire Network Sensors

| | Samples | | | | | | | | |
|---|---|---|---|---|---|---|---|---|---|
| | S1 | S2 | S3 | S4 | S5 | S6 | S7 | S8 | S9 |
| $d_{Cr}$ (nm) | 2 | 3 | 3 | 2 | 1 | 2 | 2 | 2 | 2 |
| $d_{Pd}$ (nm) | 2 | 2 | 2 | 4 | 2 | 3 | 4 | 6 | 7 |
| $R_0$ (kΩ) | 5.941 | 3.038 | 2.235 | 1.290 | 7.806 | 3.800 | 1.284 | 0.826 | 0.381 |

Figure 7:
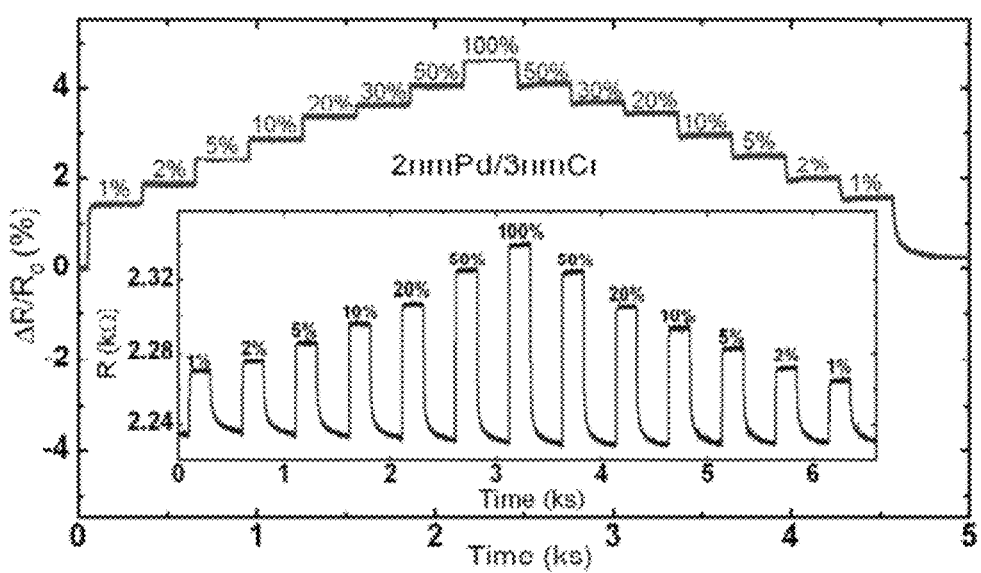
FIG. 7 shows responses of 2 nm Pd/3 nm Cr nanowire networks to hydrogen gas of various concentrations. $\Delta R$ is defined as the absolute resistance change $R(t)-R_0$ where $R_0$ is the baseline resistance in the absence of hydrogen gas. The data presented in the main panel and in the inset are from Samples S2 and S3, respectively.

$d_{Cr}$ and $d_{Pd}$ are the nominal thicknesses of the deposited Cr and Pd layers, respectively The resistance of a network of pure Pd nanowires was found to decrease (or decrease after an initial positive surge) in the presence of $H_2$ when its thickness was reduced to less than 7 nm.[37] That is, its $H_2$ responses are dominated (or affected) by broken Pd nanowires which can become continuous and more conductive due to hydrogen-induced dilation of Pd grains.[13,37] However, in our Pd/Cr nanowire networks, which consist of a Pd layer thinner than 7 nm, the resistance increases when exposed to various concentrations of $H_2$, as indicated by the data presented in FIG. 7 for Samples S2 and S3 based on a 2 nmPd/3 nmCr network. It is evident that the resistance of the sample initially increases with time and then saturates at a value that depends on the $H_2$ concentration. Experimentally we did not observe hydrogen induced resistance changes in the control samples (Samples C1-C4) with only Cr deposited on both filtration membranes and Si substrates. Furthermore, a gap closing between neighboring Pd clusters or Pd and Cr clusters due to the dilation of Pd clusters in the presence of hydrogen will decrease the resistance of the nanowires. Thus, the observed resistance increase of the Pd/Cr nanowire networks should originate from the formation of Pd/H solid solution (at low $H_2$ concentrations) or Pd hydride (at high concentrations).[9,26,27,37] This also implies that the Pd nanowire networks are continuous.

Figure 8:
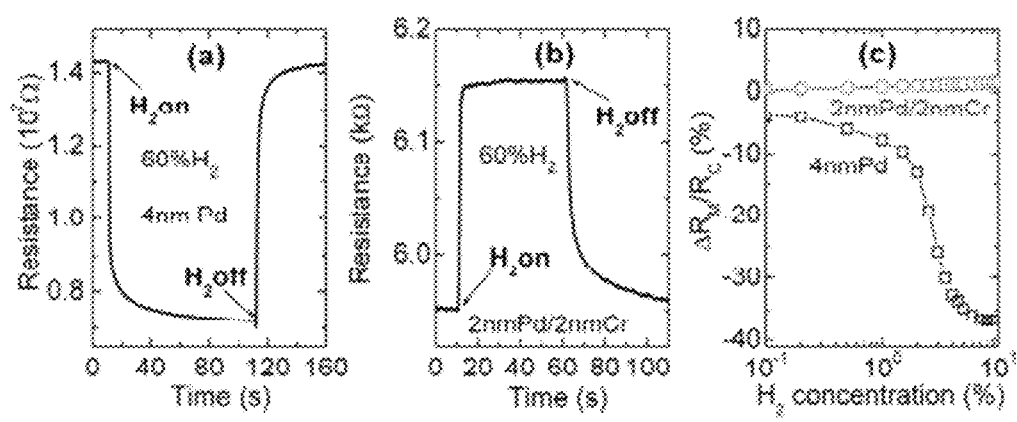
FIG. 8 shows comparisons of the hydrogen responses of a bare 4 nm Pd (Sample C5) and a 2 nm Pd/2 nm Cr (Sample S1) nanowire network which have the same total thicknesses: (a) and (b) are the evolution of the resistance with time at a fixed concentration of 60% and (c) gives the maximal resistance change $\Delta R_M/R_0$ at various concentrations. $R_0$ is the baseline resistance in the absence of hydrogen gas and $\Delta R_M$ is defined as the maximal resistance change $\Delta R=R(t)-R_0$ at the steady state for a specific concentration.

The dramatic effect of the Cr buffer layer on the performance of the Pd-based network sensors can be clearly seen in FIG. 8 which present a comparison of the $H_2$ responses for a 4 nm thick Pd nanowire network (Sample C5) with a 2 nmPd/2 nmCr network (Sample S1). Although the total thicknesses of these two networks are identical, their baseline resistances in the absence of $H_2$ differ by a factor of more that three orders of magnitudes: the resistance of the 4 nm Pd sample is as high as 10 MΩ while the replacement of 2 nm thick Pd with a 2 nm thick Cr layer reduces the resistance to a few kΩ, as shown by the data presented in FIGS. 8a and 8b and Tables I and II. Since Cr has higher electrical resistivity than Pd,[46,47] such an enormous reduction of the sample resistance by the Cr layer implies a change in the morphology of the Pd/Cr nanowires from that of the pure Pd ones. That is, the 4 nm thick pure Pd network probably consists of broken nanowires while the 2 nmPd/2 nmCr networks should be continuous. Such a change in morphology is reflected in the $H_2$ responses: the resistance of the 2 nmPd/2 nmCr sample (Sample S1) increases when exposed to $H_2$, in contrast to that of the 4 nm thick pure Pd sample (Sample C5) for the same $H_2$ concentration, as indicated by the data presented in FIG. 8a and FIG. 8b. The same behavior was observed for all tested $H_2$ concentrations, as demonstrated by the concentration dependences of the maximal resistance change $\Delta R_M/R_0$ given in FIG. 8c for these two samples.

The above results clearly indicate that the Pd layer with a nominal thickness of only 2 nm is electrically connected in the Pd/Cr nanowires. This could be understandable if the Cr adhesion layer were continuous, resulting in a continuous Pd layer on top of it due to the complete wettability between two metals. Although a layer by layer growth of Cr films on alumina substrates with perfect surfaces was observed, a reduced surface promotes a three-dimensional (3D) growth process.[48] These results were attributed to the strong chemical interaction between Cr and the alumina surface, and to the 3D nucleation on defect sites.[48] The extremely high resistances of our control samples with a Cr thickness of 2 nm or less on filtration membranes (Samples C1 and C2 in Table II) indicate that broken Cr nanowires dominate their electrical properties. This implies that the Cr layer on alumina filtration membrane probably grows via a 3D nucleation process and may not be continuous when its thickness is 2 nm or less. Due to the strong chemical interaction between Cr and the alumina surface,[48] however, the Cr clusters should spread over a lager area than the Pd clusters for the same nominal layer thickness. Since the Pd on top of Cr will be continuous and it will be easier to fill the small gaps between neighboring Cr clusters with Pd, this can lead to a decrease of the total thickness required to form continuous Pd nanowires. That is, a Cr layer of 2 nm or less in the Pd/Cr nanowires on the filtration membrane promotes the formation of a continuous Pd layer with a thickness less than that required in pure Pd nanowires, even though the Cr layer itself may be discontinuous. Furthermore, the Pd and Cr (or parts of them) may also form an alloy, similar to that observed in the Ni/Cr alloy,[42,43] which can have improved wettability on the filtration membrane than pure Pd, leading to a reduction in the critical thickness requirement for forming continuous Pd/Cr nanowires. It is clear that more research is needed to reveal the mechanism responsible for the reduction of the critical thickness induced by the Cr adhesion layer for forming continuous Pd and Pd/Cr layers.

TABLE II

Baseline Resistances ($R_0$) of the Comparison Samples

| | Samples | | | | | | |
|---|---|---|---|---|---|---|---|
| | C1 | C2 | C3 | C4 | C5 | C6 | C7 |
| Substrates | Filter | Filter | Filter | Si | Filter | Filter | Si |
| $d_{Cr}$ (nm) | 1 | 2 | 3 | 1 | 0 | 0 | 2 |
| $d_{Pd}$ (nm) | 0 | 0 | 0 | 0 | 4 | 7 | 2 |
| $R_0$ (kΩ) | 8500 | 2600 | 28.10 | 2.401 | 14290 | 2.089 | 0.123 |

$d_{Cr}$ and $d_{Pd}$ are the nominal thicknesses of the deposited Cr and Pd layers, respectively When bulk Pd is exposed to hydrogen,[49] it forms a Pd/H solid solution (α-phase) and a Pd hydride (β-phase) at hydrogen contents (atomic ratios of H:Pd) less than $\alpha_M$ and higher than $\beta_m$, respectively. At room temperature the values of $\alpha_M$ and $\beta_m$ are 0.015 and 0.61, respectively. A mixed phase (α+β phase) exists at intermediate hydrogen content. The hydrogen induced resistance change, which is the core of a Pd based resistive $H_2$ sensor, is very sensitive to the hydrogen content in the α phase and shows only a small increase from $\alpha_M$ up to $\beta_m$ composition. In the β phase region, the resistance first increases abruptly, reaching a value of 87% larger at ~β=0.76 and then stays nearly constant at higher hydrogen contents. The $H_2$ concentration dependence of the resistance change in thick Pd films follows a similar trend with the appearance of the pure β phase at concentrations of 1-1.5%, depending on the thickness of the film.[36] Since the resistance of Pd in majority portion of the pure β phase does not change with $H_2$ concentration, a pure Pd based sensor loses its sensitivity and thus, is inapplicable at high $H_2$ concentrations (>2%).

Such saturation behavior was also reported for electrodeposited single Pd nanowires[26,27] and for networks of pure Pd nanowires formed on filtration membranes[37] where the sample resistance first increases with $H_2$ concentration up to about 1-2% and then remains constant at higher concentrations. The data shown in FIG. 7 for the 2 nmPd/3 nmCr nanowire network, however, clearly show a difference in the resistance change induced by hydrogen with concentrations up to 100%. This observation is further summarized in FIG. 9a where we plot the resistance change obtained at various $H_2$ concentrations. Quantitative analysis demonstrates that the concentration dependence of the maximal resistance change $\Delta R_M/R_0$ follows a power-law relation with an exponent of 0.26 for concentrations up to 100%. This indicates that the interaction of $H_2$ and Pd in the whole concentration range follows Sievert's law.[50] That is, the ratio of the dissolved atomic $H_2$ to Pd atoms can be described to a good approximation with a power-law dependence of the $H_2$ partial pressure (i.e. $H_2$ gas concentrations in our experiments) and the change of this ratio leads to a proportional $\Delta R_M/R_0$ response.[50] The exponent of n=0.26 is smaller than the theoretical value of 0.5 and that (0.58) for a 7 nm thick pure Pd nanowire network.[37] This difference can be partially attributed to the $H_2$ insensitive resistance of the shunted Cr layer. This hypothesis is consistent with the observed exponent increase when the resistance contributed by the Cr layer is smaller, as demonstrated by the data obtained by either reducing the thickness of the Cr layer from 3 nm to 1 nm while keeping the thickness of the Pd layer at 2 nm (inset of FIG. 9b) or increasing that of the Pd (FIG. 10a) from 2 nm to 6 nm as the Cr layer stays at 2 nm thick. However, the change of n (from 0.28 to 0.68) induced by increasing the thickness of the Pd layer is much larger than that (from 0.26 to 0.33) by decreasing the thickness of the Cr layer, though the changes in the ratios of the thicknesses of Pd and Cr layers are the same.

This indicates that the exponent n is strongly associated with the confinement effect due to the thickness reduction in the Pd layer.

Figure 9:
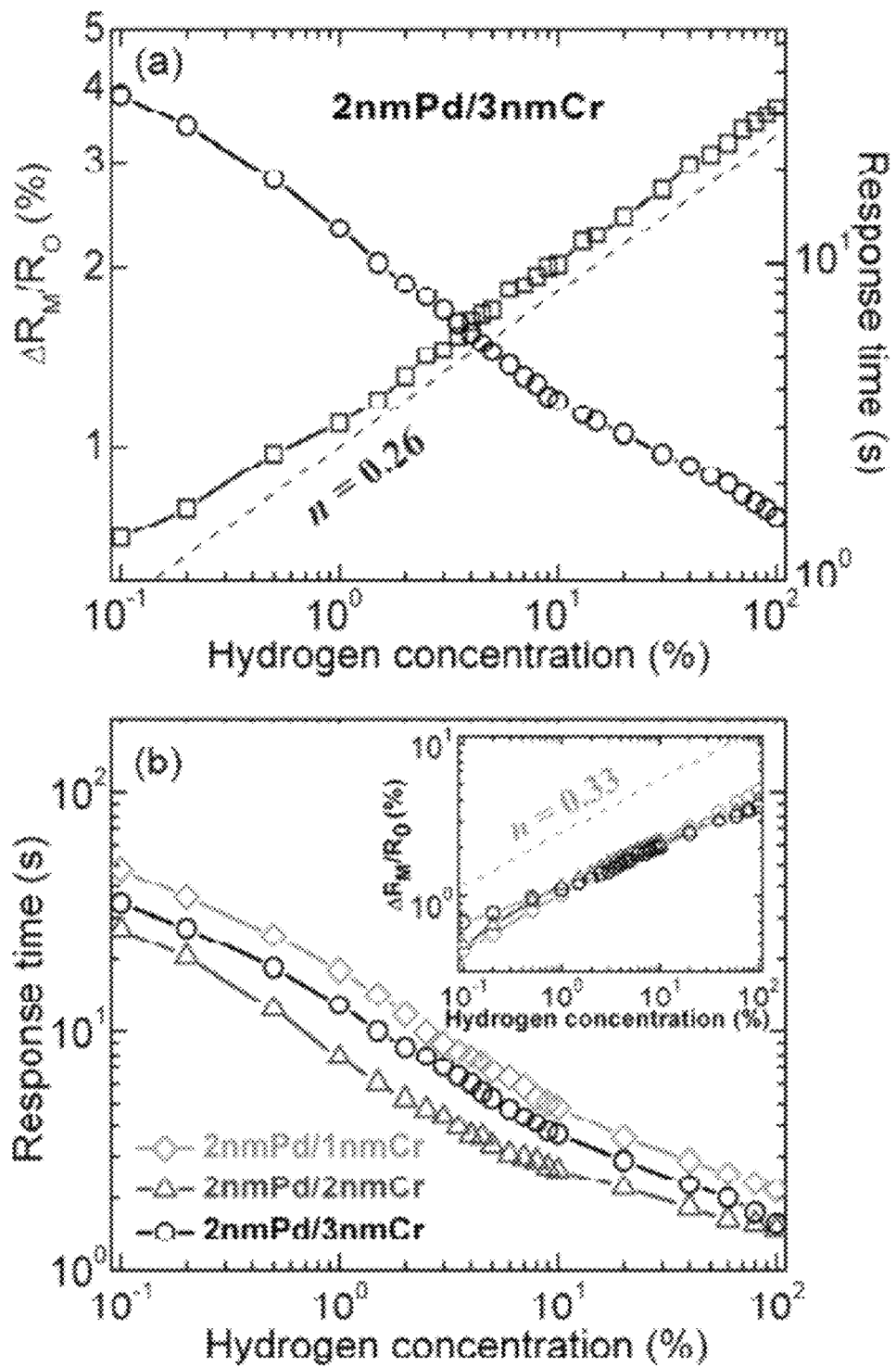
FIG. 9 shows concentration dependences of the response times and the maximal resistance changes $\Delta R_M/R_0$ for a 2 nm Pd/3 nm Cr nanowire network (Sample S3) (a) and 2 nm Pd/1 nm Cr (Sample S5), 2 nm Pd/2 nm Cr (Sample S1) and 2 nm Pd/3 nm Cr (Sample S3) (panel (b) and its inset). The response time is defined as the rise time to reach 90% of its maximal change, i.e. $\Delta R/\Delta R_M=0.9$. The dashed lines in (a) and in the inset of (b) represent a power-law relation with exponents of n=0.26 and 0.33, respectively.

The power-law dependence of the resistance change on the $H_2$ concentration implies that the 2 nm thick Pd nanowire network is in the α-phase for the whole concentration range and that the addition of a Cr buffer layer suppresses the α to β phase transition. The absence of the β phase can also be inferred from the concentration dependence of the response time, which is defined as the rise time to reach 90% of its maximal change, as presented in FIG. 9b for a series of Pd/Cr nanowire networks with various Cr layer thicknesses of 1 nm, 2 nm and 3 nm. A peak or bump in the response time versus concentration relation was found to accompany the α to β phase transition in single Pd nanowires[25,26] and pure Pd nanowire networks.[37] However, the data in FIG. 9b show a monotonic decrease of the response time with $H_2$ concentration up to 100%.

Figure 10:
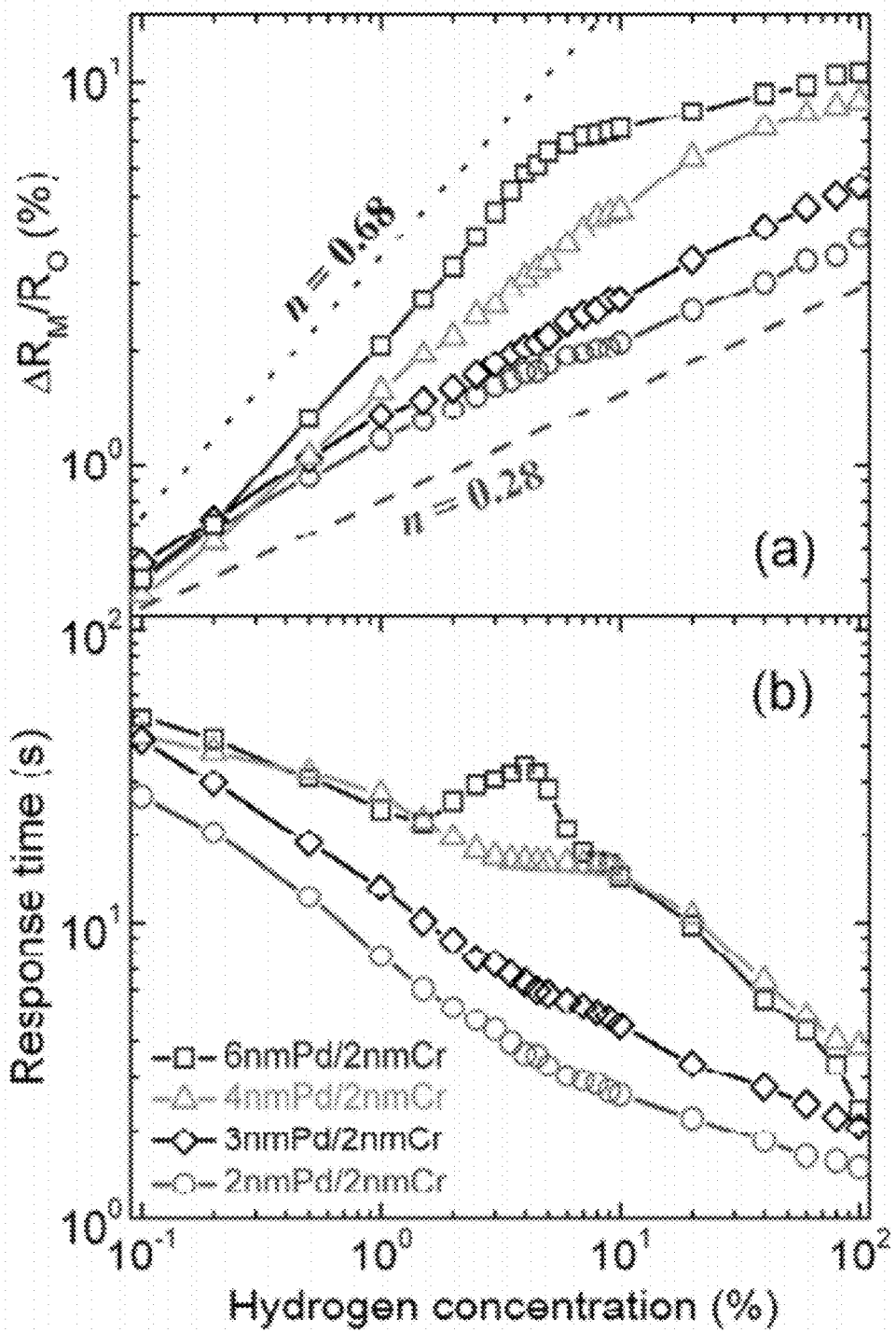
FIG. 10 shows concentration dependences of the maximal resistance change $\Delta R_M/R_0$ (a) and the response times (b) for 2 nm Pd/2 nm Cr (Sample S1), 3 nm Pd/2 nm Cr (Sample S6), 4 nm Pd/2 nm Cr (Sample S7), and 6 nm Pd/2 nm Cr (Sample S8) nanowire networks. The dashed and dotted lines in (a) represent a power-law relation with exponents of n=0.28 and 0.68, respectively.

The survival of the α-phase at high $H_2$ concentrations can be a consequence of confinement effect. In fact, x-ray diffraction measurements on Pd-nanoclusters reveal no α to β phase transition in 3.8 nm sized clusters.[51] Hydrogen solubility studies[52] on palladium clusters with diameters of 2-5 nm also show that nanoclusters in the α phase can absorb 5-10 times more $H_2$ than bulk palladium, shifting the maximum hydrogen content ($\alpha_M$) to a higher value. Hence, the concentration range of the α-phase is extended when the cluster-size of Pd is reduced. Such an enhancement of the hydrogen solubility in the α-phase of Pd nanoclusters is attributed to the existence of subsurface sites for hydrogen atoms, in addition to the usual octahedral sites of the face-center-cubic (fcc) Pd host lattice.[52] Although Pd forms a continuous nanowire network rather than separate nanoclusters in the 2 nm Pd/3 nmCr sample, the confinement effect seems to be strong enough to sustain the α phase up to $H_2$ concentrations of 100%. Since the width (7 nm-9 nm) of the nanowires in the network is larger than the diameter (6 nm) of the nanoclusters in which α to β phase transition was observed,[47] the extension of the concentration range for the α phase is due to the confinement in the thickness direction. In this case, the β-phase is expected to appear when the thickness of the nanowire network is increased. FIG. 10 presents $H_2$ responses of Pd/Cr nanowire networks with various Pd layer thicknesses while maintaining a constant Cr buffer layer thickness. For samples with Pd thicknesses of 2 nm and 3 nm, the $H_2$ concentration dependence of the resistance change $\Delta R_M/R_0$ follows a power-law relation, and the response times also decrease monotonically with concentrations up to 100%. Thus, the α to β phase transition should be absent in the Pd/Cr nanowire networks with Pd layer thickness of 3 nm or less. When the thickness of the Pd layer is increased to 4 nm, the power-law dependence of the resistance change $\Delta R_M/R_0$ on concentration is valid up to a $H_2$ concentration of 8%. A bump also appears in the response time versus concentration curve. With further increase of the Pd thickness up to 6 nm, the deviation from the power-law relation in the $\Delta R_M/R_0$ versus concentration curve becomes more significant at $H_2$ concentration above 5%. A clear peak also emerges in the concentration dependence of the response time. These features are characteristics of the α to β phase transition and reveal the existence of the β-phase in the samples with 4 nm and 6 nm thick Pd layers. The observation of the α to β phase transition in these samples indicates that the Pd layer in the Pd/Cr networks behaves similarly to the nanoclusters,[51] electrodeposited single nanowires,[25,26] and nanowire networks[37] of pure Pd. This implies that pure Pd with at least one-dimension (e.g. thickness) of less than 4 nm could be sensitive to $H_2$ at concentrations up to 100%. Since the lattice expansion in the α-phase is extremely small, it will be extremely challenging to utilize the 'gap closing' mechanism[7,13] to detect $H_2$. As observed in both films[1,29] and nanowire networks[37] formed on bare substrates, however, a layer of pure Pd will become discontinuous when its thickness is reduced to less than 4 nm. Our success in fabricating a continuous Pd layer as thin as 2 nm by adding a thin buffer layer of Cr provides a new way to achieve Pd-based sensors, which can be sensitive to $H_2$ at concentrations of up to 100%.

Figure 11:
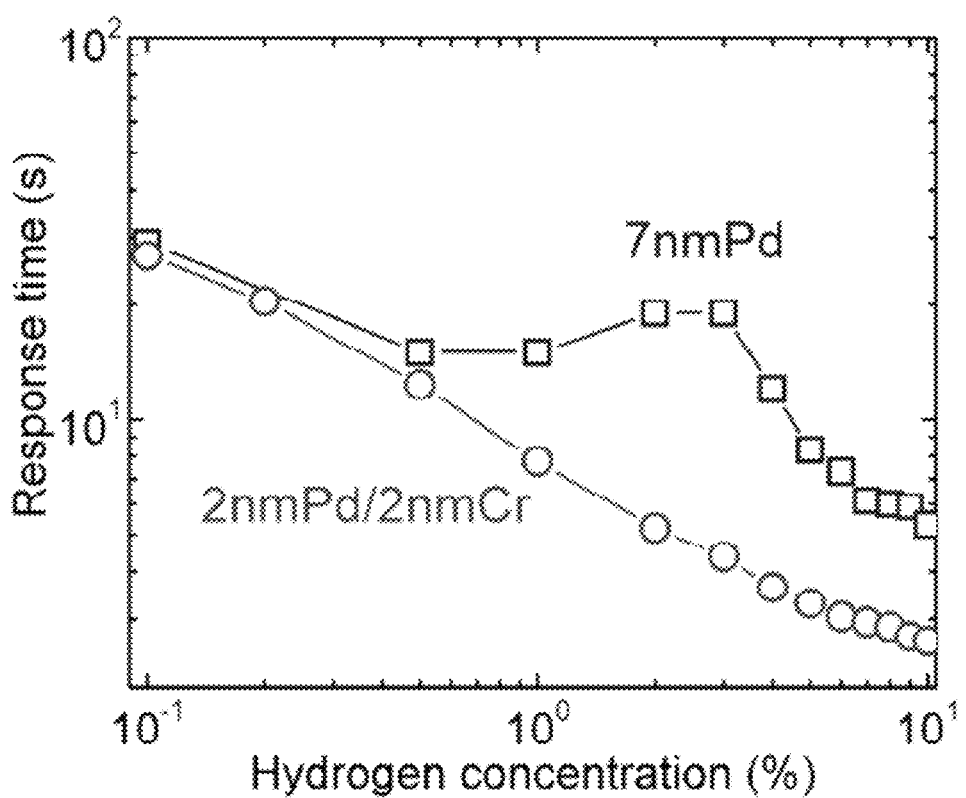
FIG. 11 shows comparison of the response times of a 2 nm Pd/2 nm Cr network (Sample S1) with a bare 7 nm Pd nanowire network (Sample C6) at various concentrations.
Figure 12:
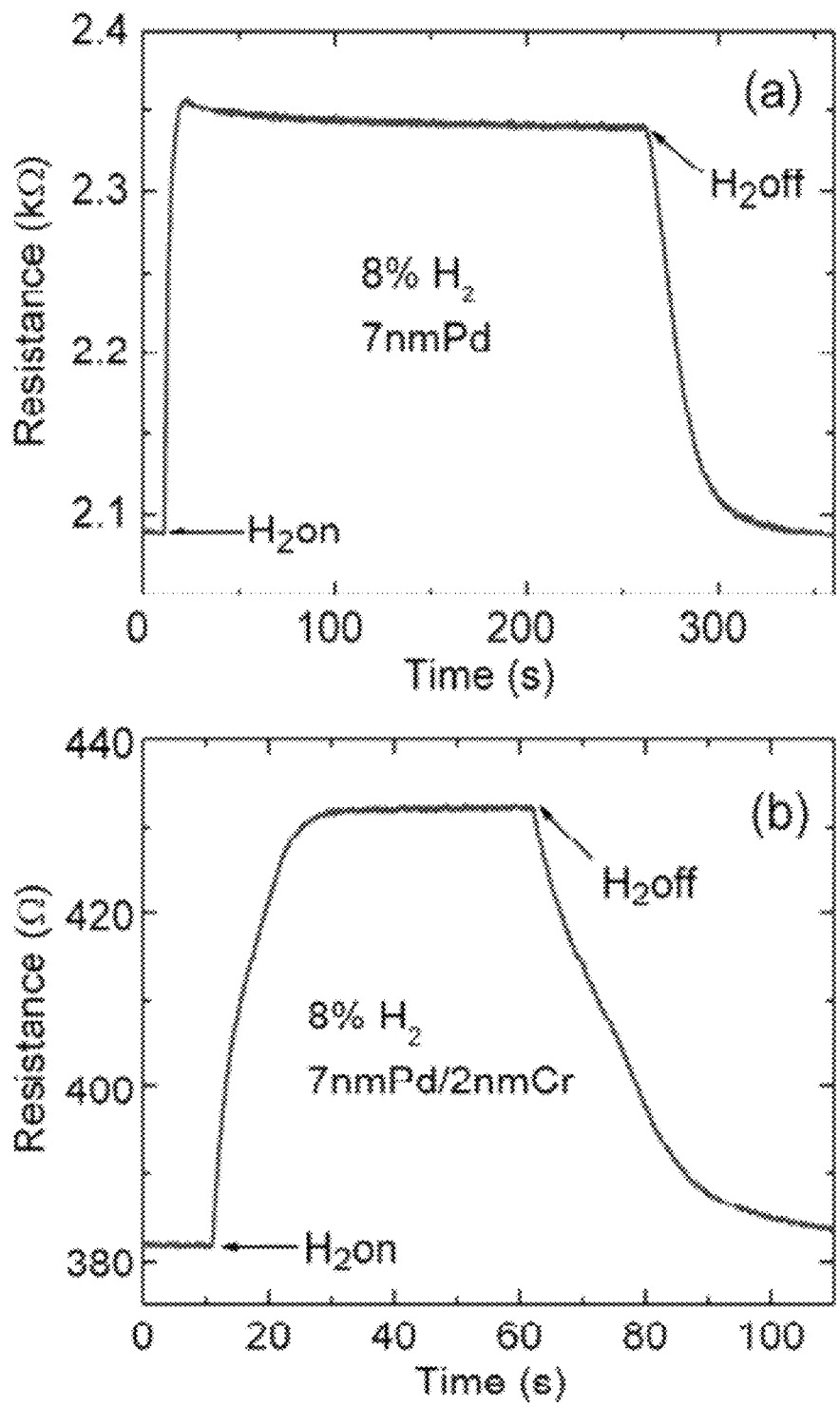
FIG. 12 shows comparison of the responses of a bare 7 nm Pd (Sample C6) (a) and a 7 nm Pd/2 nm Cr (Sample S9) (b) nanowire networks to 8% $H_2$.

It has been demonstrated in both single Pd nanowires[26] and Pd nanowire networks[37] that the surface area to volume (SA/V) ratio limits the response time of the sensor rather than the proton diffusion. This is because the proton diffusion time in a nanostructure is far shorter than any reported sensor response time. For example, Einstein's expression[26] yields a time of ~100 μs for a proton to diffuse a distance of 10 nm. FIG. 11 presents a comparison of the fastest response times observed in a 2 nmPd/2 nmCr network and in a pure 7 nm thick Pd network. Though the 2 nm thick Pd network is indeed faster at all tested concentrations, the difference in the response times is definitely much shorter than that (by a factor of ~12) expected from a diffusion limited process. Furthermore, the long response times in the 7 nm thick nanowire network at $H_2$ concentrations above 1% reflect a significant contribution from the α top β phase transition which causes a retarded $H_2$ response.[25,26] The difference (a factor of 1.08-1.21) in response times for these two samples in the α phase (at $H_2$ concentrations less than 1%) is also smaller than that expected due to SA/V ratio increase (a factor of 1.82-1.98 by assuming a rectangular cross-section for the Pd nanowires with a width of 7-9 nm). This disparity is probably caused by the reduction of granularity in the 2 nm thick Pd nanowire network with a Cr buffer layer. The 7 nm thick Pd sample deposited on a bare oxide substrate should be more granular and the grain boundaries serve as additional surfaces to interact with hydrogen. This hypothesis is in fact supported by the data presented in FIG. 12: at a hydrogen concentration of 8%, the resistance of a 7 nm thick Pd nanowire network with a 2 nm thick buffer layer of Cr remains constant between 30 and 60 seconds, while that for the sample on bare substrate cannot reach a steady state after more than 250 s. The decrease of the resistance with time at a constant hydrogen concentration indicates that the 7 nm thick Pd nanowire network without a 2 nm thick buffer layer of Cr is granular and the hydrogen-induced Pd grain dilation enables more conducting paths when more gaps between neighboring grains are shortened with time.

Figure 13:
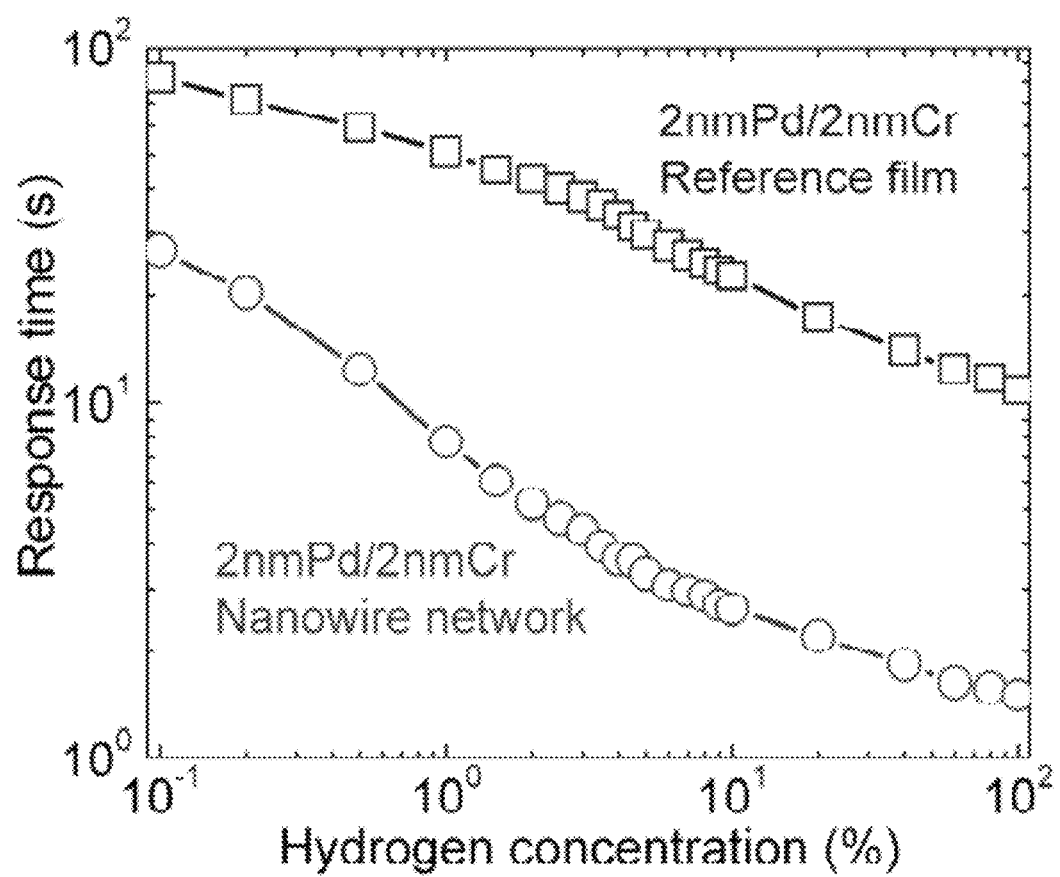
FIG. 13 shows comparison of the response times of a 2 nm Pd/2 nm Cr network (Sample S1) with its reference film (Sample C7) at various concentrations.

The importance of surface area on the sensor response time is further demonstrated in FIG. 13 where we compare the response times of a 2 nmPd/2 nmCr nanowire network and its reference film deposited simultaneously onto a silicon substrate (with a 300 nm thick oxide top layer). Since the shortest hydrogen diffusion distance of 2 nm (the thickness) is the same for both samples, the significant decrease of the response times in the network sample must come from the additional surface area of the porous substrate morphology. As discussed above, the growth mode of a Cr film can strongly depend on the roughness of the substrate surface.[48] In fact, this can be the origin of the pronounced difference in resistances of the 1 nm thick Cr samples deposited on a filtration membrane and a Si substrate (Samples C1 and C4 in Table II, respectively). That is, the morphology of the Pd layers on Cr coated filtration membrane and Si substrate may not exactly be identical, resulting in different $H_2$ absorption kinetics. This could account for the dependence of the response times on $H_2$ concentration ratios in these two types of samples, as demonstrated by the data given in FIG. 13.

Figure 14:
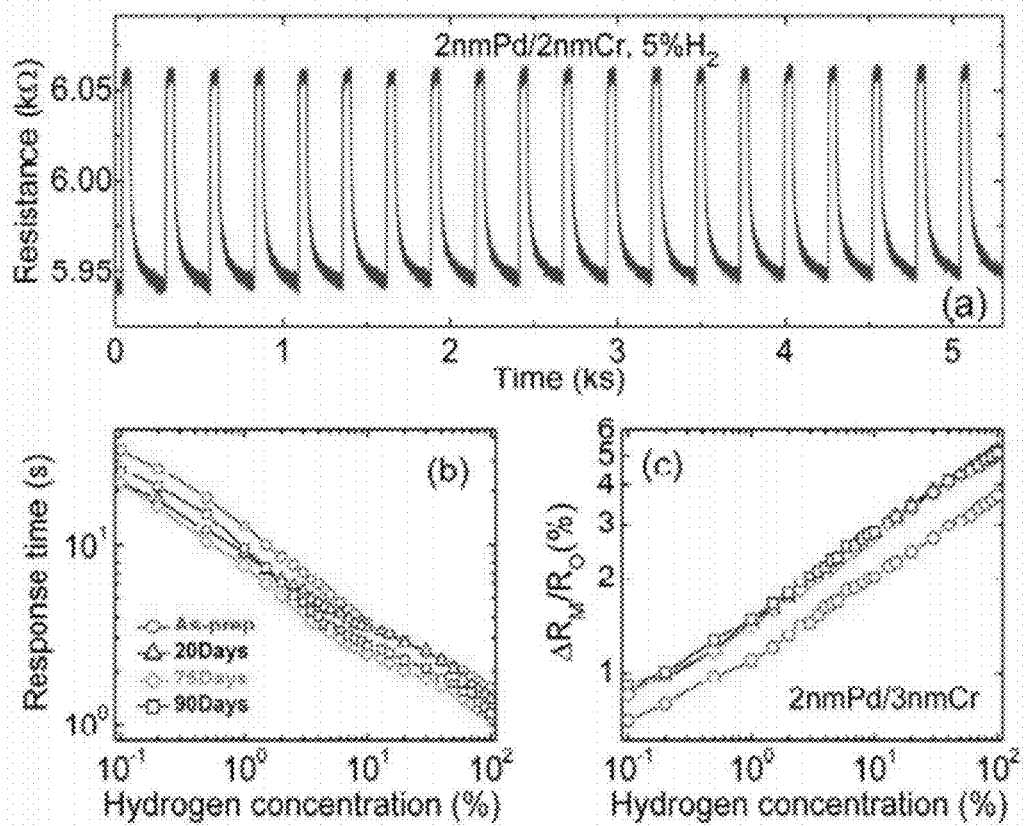
FIG. 14 illustrates data on the reversibility and durability: (a) Responses of a 2 nm Pd/2 nm Cr nanowire network (Sample S1) to 5% hydrogen for 20 cycles. (b) Hydrogen concentration dependences of the response times and the maximal resistance changes $\Delta R_M/R_0$ of a 2 nm Pd/3 nm Cr nanowire network (Sample S3) obtained shortly (within hours) after fabrication and stored in air for 20, 75 and 90 days.

Ostwald ripening, in which the larger clusters take up mobile atoms at the expense of smaller ones in a nanocluster ensemble is an extremely slow process at room temperature. However, the presence of a hydrogen atom in the metal lattice reduces the binding energy, thus increasing the probability of detachment of palladium atoms.[53] Recently Di Vece et al. reported hydrogen-induced Ostwald ripening at room temperature in a Pd nanocluster film.[53] Such a ripening process could also occur in our sputter-deposited Pd nanowire networks consisting of grains of various sizes, leading to irreversible hydrogen responses due to a morphological or structural change during a hydrogenation of the network. FIG. 14a shows a resistance versus time curve for a 2 nmPd/2 nmCr nanowire network (Sample S1) with 20 loading/unloading cycles. It is evident that the process is reversible: the resistance of the sample in the presence of hydrogen stays precisely the same for all cycles while it increases slightly when the hydrogen is replaced with nitrogen, probably due to the slow recovery which may require an even longer waiting time. This result, along with data presented in the inset of FIG. 7 showing repeatable resistance change during hydrogen concentration sweeping, demonstrate that our Pd/Cr nanowire networks can respond to hydrogen reversibly, excluding the occurrence of Ostwald ripening. We also did not observe fracturing of the Pd/Cr nanowires after repeated exposures to $H_2$, in contrast to that reported for pure Pd nanowires.[22] This robustness of the Pd/Cr sensor may be a benefit of the strong chemical interaction between Cr and the alumina surface.[48]

In many applications a hydrogen sensor needs to be exposed to air or an oxygen environment. Though the Cr layer is covered by the Pd layer on the top surface, it may oxidize by reacting with oxygen diffused in from the sides. Such a process in the Cr layer might have an impact on the morphology of the Pd layer and hence on the performance of the Pd/Cr hydrogen sensor. We addressed this issue by examining the hydrogen responses of a 2 nmPd/3 nmCr sensor (Sample S3) just after preparation (and stored in a drybox for a few hours to make electrical contacts) and exposed to air for various periods of time. The results are presented in FIGS. 14b and 14c. Surprisingly, after storage in air the sensor has a larger resistance change and a shorter response time compared to those of the pristine sample. That is, the performance of the sensor is improved by exposure to air. This indicates that due to the oxidation of the Cr layer the Pd layer may have more defects which can act as additional hydrogen interaction 'surfaces'. The oxidation process, however, should end after a period of time. Thus the sensor should become stable eventually, as demonstrated by the nearly identical resistance changes of the sensor stored in air after 20, 75 and 90 days (see FIG. 14c). The slight difference in the concentration dependence of the response times obtained after 20 days or longer air exposure indicates subtle changes in the sensor.

Figure 15:
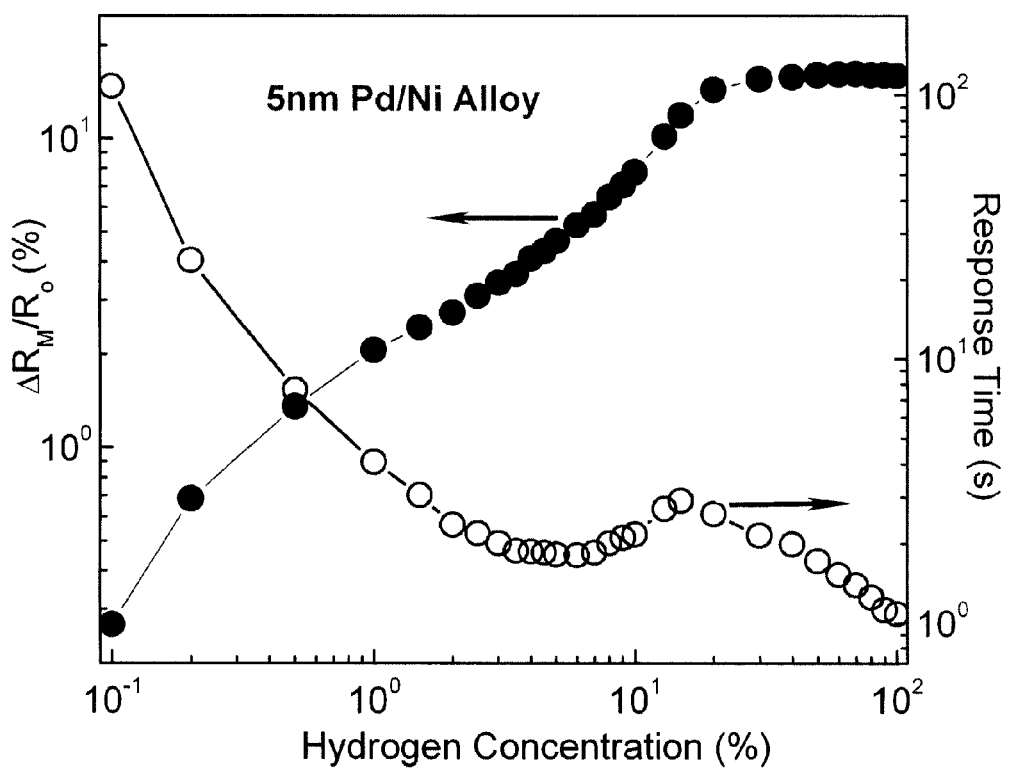
FIG. 15 presents the concentration dependences of the maximal resistance change and the response time of a 5 nm thick Pd/Ni alloy nanowire network (the nominal Ni content is 6%).

A 5 nm thick Pd/Ni alloy nanowire network (the nominal Ni content is 6%) was formed in the same manner as the nanowire networks described above. FIG. 15 presents the concentration dependences of the maximal resistance change and the response time of this 5 nm thick Pd/Ni alloy nanowire network.

Figure 16:
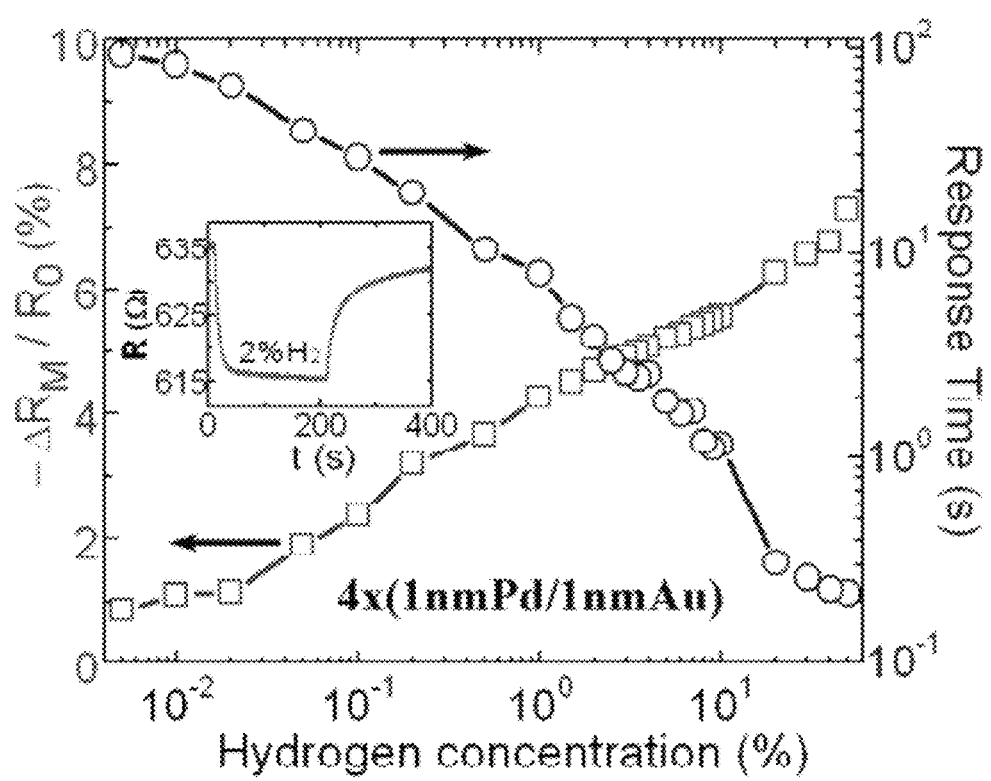
FIG. 16 illustrates $H_2$ responses of a network of 4×(1 nmPd/1 nmAu) multilayer nanowires. The inset presents the real time resistance evolution at 2% $H_2$.

An 8 layer nanowire network, formed of alternating layers of Au and Pd was also formed in the same manner as the nanowire networks described above. FIG. 16 illustrates $H_2$ responses of this network of 4×(1 nmPd/1 nmAu) multilayer nanowires. The inset presents the real time resistance evolution at 2% $H_2$.

Fabrication of Pd/Cr Nanowire Networks.

Commercially available Anodisc® 13 membranes (Whatman Company)[41] with a nominal filtration pore diameter of 20 nm were cleaned in acetone for 10 min in an ultrasonic bath and then rinsed with deionized water followed with an ethanol rinse. They were dried using high-purity nitrogen gas.[37] Cr and Pd were sputtered sequentially onto the filtration membrane surface by employing an AJA ACT-2400 thin film deposition system under a base vacuum of $\sim 1 \times 10^{-7}$ Torr. The working gas was argon (Ar) at a pressure of 3 mTorr. The deposition rates of Cr and Pd were 0.49 Å/s and 1.3 Å/s respectively, determined by an in-situ quartz crystal microbalance (QCM) thickness monitor (model TM-350 from Maxtek, Inc.). The sputtering time for a deposited metal was defined by using a desired nominal thickness divided by the deposition rate. A reference film was prepared for each nanowire network sample by placing a silicon substrate (with an oxide top layer of 300 nm) nearby during sputtering.

Scanning Electron Microscopy (SEM).

A high-resolution field emission scanning electron microscope (FESEM) (Hitachi S-4700II) was used to image the morphology of the fabricated samples. The samples were mounted on an aluminum holder with double-sided carbon tape. The sample's top surface coated with Pd/Cr was also connected to the sample holder with double-sided carbon tape to avoid charging effects.

Hydrogen Sensing.

Rectangle-shaped samples with width of 2±0.5 millimeters were cut from the Pd/Cr coated filtration membrane and glued onto a sample holder with the Pd/Cr nanowire networks facing up. Four electrical contacts were made to the sample with silver paste and the distances between the two voltage leads are 3±1 millimeters.[37] The $H_2$ sensor testing was performed by placing the sample in a sealed flow cell with a total dead volume of 2-3 mL. An array of ultrafast solenoid valves (response time of 25 ms) and minimized dead volume of the gas passages were used to accurately characterize these sensors with response times down to tens of milliseconds. $H_2$ gas (Airgas, ultrahigh purity or with concentrations of 0.1%, 1% or 10% balanced with $N_2$) was premixed with $N_2$ gas (Airgas, ultrahigh purity) to the desired concentrations using mass flow controllers (Aalborg GFC17A). The purging gas is $N_2$. The total gas flow rate was 200 sccm. The resistance of the sample was measured in constant current mode with a current source (Keithly 6221), which can provide current from tens of nanoamperes to a few milliamperes. The voltage was recorded with a precision high-speed digital-to-analog (DAC) board (NI6259, 16 bits, sampling rate up to 1 MS/s) via a voltage preamplifier (Stanford Research Systems, SR560). All tests were carried out at room temperature.

REFERENCES

1. Ramanathan, M.; Skudlarek, G.; Wang, H. H.; Darling, S. B. Crossover Behavior in the Hydrogen Sensing Mechanism for Palladium Ultrathin Films. *Nanotechnology* 2010, 21, 125501.
2. www1.eere.energy.gov/hydrogenandfuelcells/mypp/index.html
3. Tabib-Azar, M.; Sutapun, Petrick, B. R.; Kazemi, A. Highly Sensitive Hydrogen Sensors Using Palladium Coated Fiber Optics with Exposed Cores and Evanscent Filed Interaction. *Sensors and Actuators B* 1999, 56, 158-163.
4. Crabtree, G. W.; Dresselhaus, M. S.; Buchanan, M. V. The Hydrogen Economy. *Phys. Today* 2004, 57, 39-44.
5. Jardine, A. P. Hydrogen Sensors for Hydrogen Fuel Cell Applications. www.powerpulse.net/techPaper.php?paperID=99.

6. Buttner, W. J.; Post, M. B.; Burgess, R.; Rivkin, C. An Overview of Hydrogen Safety Sensors and Requirements. *Inter. J. of Hydro. Energy* 2011, 36, 2462-2470.
7. Kong, J.; Chapline, M. G.; Dai, H. J. Functionalized Carbon Nanotubes for Molecular Hydrogen Sensors. *Adv. Mater.* 2001, 13, 1384-1386.
8. Favier, F.; Walter, E. C.; Zach, M. P.; Benter, T.; M. Penner, R. M. Hydrogen Sensors and Switches From Electrodeposited Palladium Mesowire Arrays. *Science* 2001, 293, 2227-2231.
9. Walter, E. C.; Favier, F.; Penner, R. M. Palladium Mesowire Arrays for Fast Hydrogen Sensors and Hydrogen-Actuated Switches. *Anal. Chem.* 2002, 74, 1546-1553.
10. Tibuzzi, A.; Di Natale, C.; D'Amico, A.; Margesin, B.; Brida, S.; Zen, M.; Soncini, G. Polysilicon Mesoscopic Wires Coated by Pd as High Sensitivity $H_2$ Sensors. *Sensors and Actuators B* 2002, 83, 175-180.
11. Varghese, O. K.; Gong, D.; Paulose, M.; Ong, K. G.; Dickey, E. C.; Grimes, C. A. Extreme Changes in the Electrical Resistance of Titania Nanotubes with Hydrogen Exposure. *Adv. Mater.* 2003, 15, 624-627.
12. Varghese, O. K.; Gong, D.; Paulose, M.; Ong, K. G.; Grimes, C. A. Hydrogen Sensing Using Titania Nanotubes. *Sensors and Actuators B* 2003, 93, 338-344.
13. Xu, T.; Zach, M. P.; Xiao, Z. L.; Rosenmann, D.; Welp, U.; Kwok, W. K.; Grabtree, G. W., Self-Assembled Monolayer Promoted Hydrogen Sensing of Ultra-Thin Palladium Films. *Appl. Phys. Lett.* 2005, 86, 203104.
14. Paulose, M.; Varghese, O. K.; Mor, G. K.; Grimes, C. A.; Ong, K. G. Unprecedented Ultra-High Hydrogen Gas Sensitivity in Undoped Titania Nanotubes. *Nanotechnology* 2006, 17, 398-402.
15. Ding, D. Y.; Chen, Z. Volume-Expansion-Enhanced Pinning of Nanoporous Pd Films for Detection of High-Concentration Hydrogen. *Sensor Lett.* 2006, 4, 331-333.
16. Ding, D. Y.; Chen, Z. A Pyrolytic, Carbon-Stabilized, Nanoporous Pd Film for Wide-Range $H_2$ Sensing. *Adv. Mater.* 2007, 19, 1996-1999.
17. Khanuja, M.; Varandani, D.; Mehta, B. R. Pulse Like Hydrogen Sensing Response in Pd Nanoparticle Layers. *Appl. Phys. Lett.* 2007, 91, 253121.
18. van Lith, J.; Lassesson, A.; Brown, S. A.; Schulze, M. Partridge, J. G.; Ayesh, A. A Hydrogen Sensor Based on Tunneling Between Palladium Clusters. *Appl. Phys. Lett.* 2007, 91, 181910.
19. Sun, Y.; Wang, H. H. High-Performance, Flexible Hydrogen Sensors That Use Carbon Nanotubes Decorated with Palladium Nanoparticles. *Adv. Mater.* 2007, 19, 2818-2820.
20. Kiefer, T.; Favier, F.; Vazquez-Mena, O.; Villanueva, G.; Brugger, J. A. Single Nanotrench in a Palladium Microwire for Hydrogen Detection. *Nanotechnology* 2008, 19, 125502.
21. Joshi, R. K.; Krishnan, S.; Yoshimura M.; Kumar, A. Pd Nanoparticles and Thin Films for Room Temperature Hydrogen Sensor. *Nanoscale Res. Lett.* 2009, 4, 1191-1196.
22. Yang, F.; Taggart, D. K.; Penner R. M. Fast, Sensitive Hydrogen Gas Detection Using Single Palladium Nanowires That Resist Fracture. *Nano Lett.* 2009, 9, 2177-2182.
23. Jeon, K. J.; Jeun, M.; Lee, E.; Lee, J. M.; Lee, K. I.; von Allmen, P.; Lee W. Finite Size Effect on Hydrogen Gas Sensing Performance in Single Pd Nanowires. *Nanotechnology* 2009, 19, 495501.
24. Offermans, P.; Tong, H. D.; van Rijn, C. J. M.; Merken, P.; Brongersma, S. H.; Crego-Calama, M. Ultralow-Power Hydrogen Sensing with Single Palladium Nanowires. *Appl. Phys. Lett.* 2009, 94, 223110.
25. Khanuja, M.; Kala, S.; Mehta, B. R.; Kruis, F. E. Concentration-Specific Hydrogen Sensing Behavior in Monosized Pd Nanoparticle Layers. *Nanotechnology* 2009, 20, 015502.
26. Yang, F.; Taggart, D. K.; Penner, R. M. Joule Heating a Palladium Nanowire Sensor for Accelerated Response and Recovery to Hydrogen Gas. *Small* 2010, 6, 1422-1429.
27. Yang, F.; Kung, S. C.; Cheng, M.; Hemminger, J. C.; Penner, R. M. Smaller Is Faster and More Sensitive: the Effect of Wire Size on the Detection of Hydrogen by Single Palladium Nanowires. *ACS Nano* 2010, 4, 5233-5244.
28. Agar, P.; Mehta, B. R.; Varandani, D.; Prasad, A. K.; Kamruddin, M.; Tyagi, A. K. Sensing Response of Palladium Nanoparticles and Thin Films to Deuterium and Hydrogen: Effect of Gas Atom Diffusivity. *Sensors and Actuators B* 2010, 150, 686-691.
29. Kiefer, T.; Villanueva, L. G.; Fargier, F.; Favier, F.; Brugger, J. The Transition in Hydrogen Sensing Behavior in Noncontinuous Palladium Films. *Appl. Phys. Lett.* 2010, 97, 121911.
30. Kiefer, T.; Villanueva, L. G.; Fargier, F.; Favier, F.; Brugger, J. Fast and Robust Hydrogen Sensors Based on Discontinuous Palladium Films on Polyimide, Fabricated on a Wafer Scale. *Nanotechnology* 2010, 21, 505501.
31. Zou, J.; Iyer, K. S.; Raston, C. L. Hydrogen-Induced Reversible Insulator-Metal Transition in a Palladium Nanosphere Sensor. *Small* 2010, 6, 2358-2361.
32. Lu, C.; Chen, Z, MOS Hydrogen Sensor with Very Fast Response Based on Ultra-Thin Thermal $SiO_2$ Film. *Inter. J. of Hydro. Energy* 2010, 35, 12561-12567.
33. Garzon, F. H. Development and Testing of a Miniaturized Hydrogen Safety Sensor. *Sensors and Actuators B* 2010, 148, 469-477.
34. Lee, J. M.; Lee, W. Effects of Surface Roughness on Hydrogen Gas Sensing Properties of Single Pd Nanowires. *J. of Nanoscience and Nanotechnology* 2011, 11, 2151-2154.
35. Kim, K. R.; Noh, J.-S.; Lee, J. M.; Kim, Y. J.; Lee, W. Suppression of Phase Transitions in Pd Thin Films by Insertion of a Ti Buffer Layer. *J. Mater Sci.* 2011, 46, 1597-1601.
36. Noh, J. S.; Lee, J. M.; Lee, W. Low-Dimensional Palladium Nanostructures for Fast and Reliable Hydrogen Gas Detection. *Sensors* 2011, 11, 825-851.
37. Zeng, X. Q.; Latimer, M. L.; Xiao, Z. L.; Panuganti, S.; Welp, U.; Kwok, W. K.; Xu, T. Hydrogen Gas Sensing with Networks of Ultrasmall Palladium Nanowires Formed on Filtration Membranes. *Nano Lett.* 2011, 11, 262-268.
38. Knight, B.; Clark, T. Development of Sensors for Automotive PEM-based Fuel Cells. www.lanl.gov/orgs/mpa/mpa11/FinalReportforDOESensorsContractUTRC.pdf
39. Liu, R.-J.; Crozier, P. A.; Smith, C. M.; Hucul, D. A.; Blackson, J.; Salaita, G. In situ Electron Microscopy Studies of the Sintering of Palladium Nanoparticles on Alumina During Catalyst Regeneration Processes. *Microsc. Microanal.* 2004, 10, 77-85.
40. Baker, R. T. K.; Prestridge, E. B.; McVicker, G. B. The Interaction of Palladium with Alumina and Titanium-Oxide Supports. *J. Catalysis* 1984, 89, 422-432.
41. Xiao, Z. L.; Han, C. Y.; Welp, U.; Wang, H. H.; Kwok, W. K.; Willing, G. A.; Hiller, J. M.; Cook, R. E.; Miller, D. J.; Crabtree, G. W. Fabrication of Alumina Nanotubes and Nanowires by Etching Porous Alumina Membranes. *Nano Lett.* 2002, 2, 1293-1297 and references therein.

42. Crispin R. M.; Nicholas M. The Wetting and Bonding Behaviour of Some Nickel Alloy-Alumina Systems. *J. Mater. Sci.* 1976, 11, 17-21.
43. Asthana, R.; Mileiko, S. T.; Sobczak, N. Wettability and Interface Considerations in Advanced Heat-Resistant Ni-Based Composites. *Bull. Pol. Ac.: Tech.* 2006. 54. 147-166.
44. Welp, U.; Xiao, Z. L.; Jiang, J. S.; Vlasko-Vlasov, V. K.; Bader, S.; Crabtree, G. W.; Liang, J.; Chik, H.; Xu, J. Superconducting Transition and Vortex Pinning in Nb Films Patterned with Nanoscale Hole-Arrays. *Phys. Rev. B.* 2002, 66, 212507.
45. Xiao, Z. L.; Han, C. Y.; Welp, U.; Wang, H. H.; Vlasko-Vlasov, V. K.; Kwok, W. K.; Willing, G. A.; Miller, D. J.; Hiller, J. M.; Cook, R. E.; Crabtree, G. W. Nickel Antidot Arrays on Alumina Substrates. *Appl. Phys. Lett.* 2002, 81, 2869-2871.
46. Kulkarni, A. K.; Chang, L. C. Electrical and Structural Characteristics of Chromium Thin Films Deposited on Glass and Alumina Substrates. *Thin Solid Films* 1997, 301, 17-22.
47. Matula, R. A. Electrical Resistivity of Copper, Gold, Palladium, and Silver. *J. Phys. Chem. Ref. Data* 1979, 8, 1147.
48. Ealet, B.; Robrieux, B; Gillet, E. A. Surface Analytical Study of the Formation and Adhesion of Chromium Films on Alumina. *J. Adhesion Sci. Technol.* 1992, 6, 1221-1231.
49. Sakamoto, Y.; Takai, K.; Takashima, I.; Imada, M. Electrical Resistance Measurements as a Function of Composition of Palladium-Hydrogen (Deuterium) Systems by a Gas Phase Method, *J. Phys.: Condens. Matter* 1996, 8, 3399-3411.
50. Thomas, R. C.; Hughes R. C. Sensors for Detecting Molecular Hydrogen Based on Pd Metal Alloys. *J. Electrochem. Soc.* 1997, 144, 3245-3249.
51. Suleiman, M.; Jisrawi, N. M.; Dankert, O.; Reetz, M. T.; Bahtz, C.; Kirchheim, R.; Pundt, A. Phase Transition and Lattice Expansion During Hydrogen Loading of Nanometer Sized Palladium Clusters. *Journal of Alloys and Compounds* 2003, 356-357, 644-648.
52. Sachs, C.; Pundt, A.; Kirchheim, R.; Winter, M.; Reetz, M. T.; Fritsch, D. Solubility of Hydrogen in Single-Sized Palladium Clusters, *Phys. Rev. B* 2001, 64, 075408.
53. Di Vece, M.; Grandjean, D.; Van Bael, M. J.; Romero, C. P.; Wang, X.; Decoster, S.; Vantomme, A.; P. Lievens, P. Hydrogen-Induced Ostwald Ripening at Room Temperature in a Pd Nanocluster Film. *Phys. Rev. Lett.* 2008, 100, 236105.
54. Liekus, K. J.; Zlochower, I. A.; Cashdollar, K. L.; Djordjevic, S. M.; Loehr, C. A. *J. Loss Prev. Process Ind.* 2000, 13, 377.
55. www.fuelcellsensor.com.
56. Bodzenta, J.; Burak, B.; Gacek, Z.; Jakubik, W. P.; Kochowski, S.; Urbanczyk, M. *Sens. Actuators, B* 2002, 87, 82.
57. Christofides, C.; Mandelis, A. *J. Appl. Phys.* 1990, 68, R1.
58. Chen, H.-I.; Chou, Y.-I.; Chu, C.-Y. *Sens. Actuators, B* 2002, 85, 10.
59. Wang, C.; Mandelis, A.; Garcia, J. A. *Rev. Sci. Instrum.* 1999, 70, 4370.
60. Sutapun, B.; Tabib-Azar, M.; Kazemi, A. *Sens. Actuators, B* 1999, 60, 27.
61. Pundt, A. *Adv. Eng. Mater.* 2004, 6, 11.
62. Lee, E.; Lee, J. M.; Koo, J. H.; Lee, W.; Lee, T. *Int. J. Hydrogen Energy* 2010, 35, 6984.
63. Jeon, K. J.; Lee, J. M.; Lee, E.; Lee, W. *Nanotechnology* 2009, 20, 135502.
64. Yu, S. F.; Welp, U.; Hua, L. Z.; Rydh, A.; Kwok, W. K.; Wang, H. H. *Chem. Mater.* 2005, 17, 3445.
65. Menke, E. J.; Thompson, M. A.; Xiang, C.; Yang, L. C.; Penner, R. M. *Nat. Mater.* 2006, 5, 914.
66. www.whatman.com/PRODAnoporeInorganicMembranes.aspx.
67. Narehood, D. G.; Kishore, S.; Goto, H.; Adair, J. H.; Nelson, J. A.; Gutierrez, H. R.; Eklund, P. C. *Int. J. Hydrogen Energy* 2009, 34, 952.
68. Eastman, J. A.; Thompson, L. J.; Kestel, B. *J. Phys. Rev. B* 1993, 48, 84.
69. Hughes, R. C.; Schubert, W. K. *J. Appl. Phys.* 1992, 71, 542.
70. "Hydrogen Gas Sensor", F. Favier, E. Walter, R. M. Penner, U.S. Pat. No. 7,186,381 (Mar. 6, 2007).
71. "Ultra-fast and ultra-sensitive hydrogen sensors based on self-assembly monolayer promoted 2-dimensional palladium nano-clusters", Tao Xu, Michael P. Zach, and Zhili Xiao; U.S. Pat. No. 7,171,841 (Feb. 6, 2007).
72. D. Y. Ding, Z. Chen, and C. Lu, "Hydrogen sensing of nanoporous palladium films supported by anodic aluminum oxides", *Sensors and Actuators B* 120, 182 (2006).
73. M. Hakamada, H. Nakano, T. Furukawa, M. Takahashi, and M. Mabuchi "Hydrogen Storage Properties of Nanoporous Palladium Fabricated by Dealloying" *J. Phys. Chem. C* 2010, 114, 868-873.

What is claimed is:

1. A network of nanowires, wherein
    the nanowires comprise Pd,
    each nanowire has a thickness of 4.5 to 7 nm,
    each nanowire has a width of at most 20 nm, and
    a substrate,
    wherein the nanowires are on the substrate.
2. The network of nanowires of claim 1, wherein the nanowires consist essentially of Pd.
3. The network of nanowires of claim 1, wherein the nanowires consist of Pd.
4. The network of nanowires of claim 1, wherein the nanowires further comprise a metal selected from the group consisting of Mg, Ti, Zr, Hf, V, Nb, Ta, Cr, Mo, W, Mn, Re, Fe, Ru, Os, Co, Rh, Ir, Ni, Pt, Cu, Ag, Au, Zn, Cd, Al, Ga, In, Si, Ge, Sn, Pb, Sb, Bi, a Lanthanide series metal, an actinide series metal, alloys thereof and compounds thereof.
5. The network of nanowires of claim 1, wherein the nanowires further comprise a metal selected from the group consisting of Ti, Zr, Nb, Cr, Mo, W, Fe, Ru, Co, Ni, Pt, Cu, Ag, Au, Zn, In, Al, Si, Ge, alloys thereof and compounds thereof.
6. The network of nanowires of claim 1, wherein the nanowires further comprise a metal selected from the group consisting of Ni, Cr, Ti, Ge, Mo, Au, Ce, Gd, Mg, alloys thereof and compounds thereof.
7. The network of nanowires of claim 1, wherein the nanowires further comprise a metal selected from the group consisting of Cr, Ti, Ge, Mo, alloys thereof and compounds thereof.
8. The network of nanowires of claim 1, wherein the substrate comprises alumina.
9. A sensor, comprising:
    a network of nanowires,
    a substrate, wherein the nanowires are on the substrate, and
    an ohmmeter or an integrated circuit, electrically coupled to the network of nanowires,
    wherein each nanowire has a thickness of at most 4 nm,
    each nanowire has a width of at most 20 nm,
    the nanowires comprise Pd, and
    the nanowires cannot form β-phase palladium hydride when exposed to hydrogen at room temperature.

10. The network of nanowires of claim 9, wherein the nanowires further comprise a metal selected from the group consisting of Cr, Ti, Ge, Mo, alloys thereof and compounds thereof.

11. The sensor of claim 9, wherein the nanowires consist essentially of Pd.

12. The sensor of claim 9, wherein the sensor is a hydrogen sensor.

13. The sensor of claim 9, wherein the sensor senses a change in hydrogen concentration from 0 to 100%.

14. The sensor of claim 9, wherein the substrate comprises alumina.

15. An electronic device, comprising:
a network of nanowires and a substrate,
wherein the nanowires comprise Pd,
each nanowire has a thickness of at most 20 nm,
each nanowire has a width of at most 20 nm,
wherein the nanowires are on the substrate, and
the electronic device is a computer, a mobile phone, a vehicle, a fuel cell, or a hydrogen storage tank.

16. The network of nanowires of claim 15, wherein each nanowire has a thickness of at most 10 nm.

17. The sensor of claim 15, wherein the nanowires consist essentially of Pd.

18. The sensor of claim 15, wherein the nanowires consist of Pd.

19. The network of nanowires of claim 15, wherein the nanowires further comprise a metal selected from the group consisting of Cr, Ti, Ge, Mo, alloys thereof and compounds thereof.

20. The electronic device of claim 15, wherein each nanowire has a thickness of 4.5 to 7 nm.

21. The electronic device of claim 15, wherein the substrate comprises alumina.

* * * * *

UNITED STATES PATENT AND TRADEMARK OFFICE
CERTIFICATE OF CORRECTION

| | | |
|---|---|---|
| PATENT NO. | : 8,839,659 B2 | Page 1 of 1 |
| APPLICATION NO. | : 13/245674 | |
| DATED | : September 23, 2014 | |
| INVENTOR(S) | : Zhili Xiao | |

It is certified that error appears in the above-identified patent and that said Letters Patent is hereby corrected as shown below:

Title Page:

Page 2. References Cited: Item (56)

Col. 1, Line 47, please delete "aspest" and insert --aspect--

Col. 2, Line 9, please delete "15461553," and insert --1546-1553,--
Col. 2, Line 48, please delete "Jean," and insert --Jeon,--

In the Claims:

Col. 24, Line 32, please delete "a substrate" and insert --the network of nanowires comprises a substrate--

Signed and Sealed this
Eleventh Day of August, 2015

Michelle K. Lee
*Director of the United States Patent and Trademark Office*